(12) United States Patent
Prior et al.

(10) Patent No.: US 12,383,352 B2
(45) Date of Patent: Aug. 12, 2025

(54) ENDOLUMINAL ROBOTIC (ELR) SYSTEMS AND METHODS

(71) Applicant: Covidien LP, Mansfield, MA (US)

(72) Inventors: Scott J. Prior, Branford, CT (US); Arvind Rajagopalan Mohan, Dracut, MA (US); John W. Komp, Dillon, CO (US); William J. Peine, Ashland, MA (US); Scott E. M. Frushour, Boulder, CO (US); Chad A. Pickering, Woburn, MA (US); Evgeni Kopel, Barkan (IL); Anthony B. Ross, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1011 days.

(21) Appl. No.: 17/396,759

(22) Filed: Aug. 8, 2021

(65) Prior Publication Data
US 2022/0047339 A1    Feb. 17, 2022

Related U.S. Application Data

(60) Provisional application No. 63/064,938, filed on Aug. 13, 2020.

(51) Int. Cl.
*A61B 17/00* (2006.01)
*A61B 1/00* (2006.01)
(Continued)

(52) U.S. Cl.
CPC .......... *A61B 34/30* (2016.02); *A61B 1/00009* (2013.01); *A61B 1/00149* (2013.01);
(Continued)

(58) Field of Classification Search
CPC . A61B 34/76; A61B 1/00009; A61B 1/00149; A61B 17/0469; A61B 2034/107;
(Continued)

(56) References Cited

U.S. PATENT DOCUMENTS 4,202,352 A   5/1980  Osborn
5,234,443 A   8/1993  Phan et al.
(Continued)

FOREIGN PATENT DOCUMENTS

BR   0013237 A   7/2003
BR   0116004 A   6/2004
(Continued)

OTHER PUBLICATIONS

Zhuoqi Cheng et all, Design and Integration of Electrical Bio-impedance Sensing in Surgical Robotic Tools for Tissue Identification and Display, Jul. 17, 2019, Frontiers in Robotics and AI, vol. 6 2019, DOI: 10.3389/frobt.2019.00055 (Year: 2019).*

(Continued)

*Primary Examiner* — Masud Ahmed
(74) *Attorney, Agent, or Firm* — Weber Rosselli & Cannon LLP

(57) ABSTRACT

Endoluminal robotic systems and corresponding methods include subsystems for visualization, navigation, pressure sensing, platform compatibility, and user interfaces. The user interfaces may be implemented by one or more of a console, haptics, image fusion, voice controls, remote support, and multi-system controls.

19 Claims, 9 Drawing Sheets

(51) Int. Cl.
*A61B 17/04* (2006.01)
*A61B 34/00* (2016.01)
*A61B 34/20* (2016.01)
*A61B 34/30* (2016.01)
*G16H 20/40* (2018.01)
*G16H 40/63* (2018.01)
*A61B 1/267* (2006.01)
*A61B 34/10* (2016.01)
*A61B 90/00* (2016.01)

(52) U.S. Cl.
CPC .......... *A61B 17/0469* (2013.01); *A61B 34/20* (2016.02); *A61B 34/76* (2016.02); *G16H 20/40* (2018.01); *G16H 40/63* (2018.01); *A61B 1/2676* (2013.01); *A61B 2034/107* (2016.02); *A61B 2034/2051* (2016.02); *A61B 34/25* (2016.02); *A61B 2034/301* (2016.02); *A61B 2034/303* (2016.02); *A61B 2090/064* (2016.02); *A61B 2090/365* (2016.02)

(58) Field of Classification Search
CPC ............ A61B 2034/2051; A61B 34/25; A61B 2034/301; A61B 2034/303; A61B 2090/064; A61B 2090/365; A61B 1/2676; A61B 34/30; A61B 34/20; A61B 90/98; A61B 2017/00119; A61B 2017/00203; A61B 2034/105; A61B 2034/2048; A61B 2034/2065; A61B 2090/0812; A61B 1/041; A61B 1/2736; A61B 1/307; A61B 1/3132; A61B 2090/378; A61B 2090/3941; A61B 2090/395; A61B 1/0005; A61B 1/05; A61B 34/10; A61B 17/0625; G16H 20/40; G16H 40/63; G16H 30/20; G16H 30/40
See application file for complete search history.

(56) References Cited

U.S. PATENT DOCUMENTS

| | | |
|---|---|---|
| 5,358,496 A | 10/1994 | Ortiz et al. |
| 5,445,646 A | 8/1995 | Euteneuer et al. |
| 5,993,466 A | 11/1999 | Yoon |
| 6,059,813 A | 5/2000 | Vrba et al. |
| 6,086,586 A | 7/2000 | Hooven |
| 6,325,808 B1 | 12/2001 | Bernard et al. |
| 6,530,947 B1 | 3/2003 | Euteneuer et al. |
| 6,533,784 B2 | 3/2003 | Truckai et al. |
| 6,607,552 B1 | 8/2003 | Hanson |
| 6,656,177 B2 | 12/2003 | Truckai et al. |
| 6,802,843 B2 | 10/2004 | Truckai et al. |
| 6,835,336 B2 | 12/2004 | Watt |
| 6,913,579 B2 | 7/2005 | Truckai et al. |
| 7,691,079 B2 | 4/2010 | Göbel |
| 7,806,891 B2 | 10/2010 | Nowlin et al. |
| 7,824,370 B2 | 11/2010 | Hirszowicz et al. |
| 7,947,000 B2 | 5/2011 | Vargas et al. |
| 8,052,636 B2 | 11/2011 | Moll et al. |
| 8,066,754 B2 | 11/2011 | Malewicz |
| 8,190,238 B2 | 5/2012 | Moll et al. |
| 8,335,359 B2 | 12/2012 | Fidrich et al. |
| 8,388,574 B2 | 3/2013 | Hirszowicz et al. |
| 8,600,551 B2 | 12/2013 | Itkowitz et al. |
| 8,706,184 B2 | 4/2014 | Mohr et al. |
| 8,827,934 B2 | 9/2014 | Chopra et al. |
| 8,914,150 B2 | 12/2014 | Moll et al. |
| 9,119,654 B2 | 9/2015 | Ramans et al. |
| 9,364,357 B2 | 6/2016 | Costello |
| 9,393,000 B2 | 7/2016 | Donhowe |
| 9,801,630 B2 | 10/2017 | Harris et al. |
| 9,839,481 B2 | 12/2017 | Blumenkranz et al. |
| 9,918,659 B2 | 3/2018 | Chopra et al. |
| 9,993,313 B2 | 6/2018 | Schuh et al. |
| 10,172,973 B2 | 1/2019 | Vendely et al. |
| 10,206,686 B2 | 2/2019 | Swayze et al. |
| 10,219,928 B2 | 3/2019 | Costello |
| 10,349,938 B2 | 7/2019 | Widenhouse et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,482,599 B2 | 11/2019 | Mintz et al. |
| 10,524,866 B2 | 1/2020 | Srinivasan et al. |
| 10,539,478 B2 | 1/2020 | Lin et al. |
| 10,543,048 B2 | 1/2020 | Noonan |
| 10,555,788 B2 | 2/2020 | Panescu et al. |
| 10,610,306 B2 | 4/2020 | Chopra |
| 10,631,949 B2 | 4/2020 | Schuh et al. |
| 10,638,953 B2 | 5/2020 | Duindam et al. |
| 10,639,108 B2 | 5/2020 | Romo et al. |
| 10,653,866 B2 | 5/2020 | Duindam et al. |
| 10,667,871 B2 | 6/2020 | Romo et al. |
| 10,667,875 B2 | 6/2020 | DeFonzo et al. |
| 10,674,970 B2 | 6/2020 | Averbuch et al. |
| 10,682,070 B2 | 6/2020 | Duindam |
| 10,682,192 B2 | 6/2020 | Fenech |
| 10,706,543 B2 | 7/2020 | Donhowe et al. |
| 10,709,506 B2 | 7/2020 | Coste-Maniere et al. |
| 10,716,637 B2 | 7/2020 | Kowshik et al. |
| 10,729,886 B2 | 8/2020 | Fenech et al. |
| 10,743,751 B2 | 8/2020 | Landey et al. |
| 10,744,303 B2 | 8/2020 | Duindam et al. |
| 10,751,140 B2 | 8/2020 | Wallace et al. |
| 10,765,303 B2 | 9/2020 | Graetzel et al. |
| 10,765,487 B2 | 9/2020 | Ho et al. |
| 10,772,485 B2 | 9/2020 | Schlesinger et al. |
| 10,779,803 B2 | 9/2020 | Prisco et al. |
| 10,779,898 B2 | 9/2020 | Hill et al. |
| 10,786,329 B2 | 9/2020 | Schuh et al. |
| 10,792,022 B2 | 10/2020 | Keast et al. |
| 10,792,464 B2 | 10/2020 | Romo et al. |
| 10,796,432 B2 | 10/2020 | Mintz et al. |
| 10,813,539 B2 | 10/2020 | Graetzel et al. |
| 10,820,947 B2 | 11/2020 | Julian |
| 10,820,954 B2 | 11/2020 | Marsot et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,842,575 B2 | 11/2020 | Panescu et al. |
| 10,842,581 B2 | 11/2020 | Bailey |
| 10,849,591 B2 | 12/2020 | Azizian et al. |
| 10,850,013 B2 | 12/2020 | Hsu et al. |
| 10,856,855 B2 | 12/2020 | Gordon |
| 10,881,280 B2 | 1/2021 | Baez, Jr. |
| 10,881,385 B2 | 1/2021 | Fenech |
| 10,885,630 B2 | 1/2021 | Li et al. |
| 2003/0013972 A1 | 1/2003 | Makin |
| 2004/0176751 A1* | 9/2004 | Weitzner ............... A61B 34/32 606/1 |
| 2005/0107808 A1 | 5/2005 | Evans et al. |
| 2005/0165276 A1 | 7/2005 | Belson et al. |
| 2006/0020272 A1 | 1/2006 | Gildenberg |
| 2006/0235457 A1 | 10/2006 | Belson |
| 2007/0060931 A1 | 3/2007 | Hamilton et al. |
| 2007/0135803 A1 | 6/2007 | Belson |
| 2011/0319932 A1 | 12/2011 | Avelar et al. |
| 2013/0096385 A1 | 4/2013 | Fenech et al. |
| 2013/0303945 A1* | 11/2013 | Blumenkranz ... A61M 25/0067 600/585 |
| 2014/0035798 A1 | 2/2014 | Kawada et al. |
| 2014/0052018 A1 | 2/2014 | Hawkins |
| 2014/0142719 A1 | 5/2014 | Gittard et al. |
| 2014/0235943 A1 | 8/2014 | Paris et al. |
| 2015/0148690 A1 | 5/2015 | Chopra et al. |
| 2015/0265368 A1 | 9/2015 | Chopra et al. |
| 2016/0001038 A1 | 1/2016 | Romo et al. |
| 2016/0067450 A1 | 3/2016 | Kowshik |
| 2016/0157939 A1 | 6/2016 | Larkin et al. |
| 2016/0183841 A1 | 6/2016 | Duindam et al. |
| 2016/0192860 A1 | 7/2016 | Allenby et al. |

(56) References Cited

U.S. PATENT DOCUMENTS

| | | |
|---|---|---|
| 2016/0256230 A1 | 9/2016 | Kowshik et al. |
| 2016/0270865 A1 | 9/2016 | Landey et al. |
| 2016/0270870 A1 | 9/2016 | Kowshik |
| 2016/0287344 A1 | 10/2016 | Donhowe et al. |
| 2016/0331358 A1 | 11/2016 | Gordon |
| 2016/0338783 A1 | 11/2016 | Romo et al. |
| 2016/0346930 A1 | 12/2016 | Hares |
| 2016/0374676 A1 | 12/2016 | Flanagan et al. |
| 2017/0020628 A1 | 1/2017 | Averbuch |
| 2017/0112366 A1 | 4/2017 | Duindam et al. |
| 2017/0112576 A1 | 4/2017 | Coste-Maniere et al. |
| 2017/0112588 A1 | 4/2017 | Bissing et al. |
| 2017/0151026 A1 | 6/2017 | Panescu et al. |
| 2017/0209071 A1 | 7/2017 | Zhao et al. |
| 2017/0224338 A1 | 8/2017 | Sung |
| 2017/0238795 A1 | 8/2017 | Blumenkranz et al. |
| 2017/0258309 A1 | 9/2017 | Deyanov |
| 2017/0265952 A1 | 9/2017 | Donhowe et al. |
| 2017/0273542 A1 | 9/2017 | Au |
| 2017/0273712 A1 | 9/2017 | Carlson et al. |
| 2017/0274189 A1 | 9/2017 | Smith et al. |
| 2017/0281287 A1 | 10/2017 | Au |
| 2017/0281288 A1 | 10/2017 | Au |
| 2017/0311844 A1 | 11/2017 | Zhao et al. |
| 2017/0319165 A1 | 11/2017 | Averbuch |
| 2017/0325896 A1 | 11/2017 | Donhowe et al. |
| 2018/0001058 A1 | 1/2018 | Schlesinger |
| 2018/0056040 A1 | 3/2018 | Fenech et al. |
| 2018/0064904 A1 | 3/2018 | Vargas et al. |
| 2018/0070935 A1 | 3/2018 | Fenech |
| 2018/0078318 A1 | 3/2018 | Barbagli et al. |
| 2018/0153621 A1 | 6/2018 | Duindam et al. |
| 2018/0214011 A1 | 8/2018 | Graetzel et al. |
| 2018/0214138 A9 | 8/2018 | Prisco et al. |
| 2018/0221038 A1 | 8/2018 | Noonan et al. |
| 2018/0221039 A1 | 8/2018 | Shah |
| 2018/0235565 A1 | 8/2018 | Azizian et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0280660 A1 | 10/2018 | Landey et al. |
| 2018/0325419 A1 | 11/2018 | Zhao et al. |
| 2018/0325499 A1 | 11/2018 | Landey et al. |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0076143 A1 | 3/2019 | Smith |
| 2019/0110839 A1 | 4/2019 | Rafii-Tari et al. |
| 2019/0125459 A1 | 5/2019 | Shelton, IV et al. |
| 2019/0133702 A1 | 5/2019 | Fenech et al. |
| 2019/0167366 A1 | 6/2019 | Ummalaneni et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192143 A1 | 6/2019 | Shelton, IV et al. |
| 2019/0192146 A1 | 6/2019 | Widenhouse et al. |
| 2019/0192234 A1 | 6/2019 | Gadda et al. |
| 2019/0192819 A1 | 6/2019 | Duindam et al. |
| 2019/0200984 A1 | 7/2019 | Shelton, IV et al. |
| 2019/0209016 A1 | 7/2019 | Herzlinger et al. |
| 2019/0209043 A1 | 7/2019 | Zhao et al. |
| 2019/0216447 A1 | 7/2019 | Bailey et al. |
| 2019/0216548 A1 | 7/2019 | Ummalaneni |
| 2019/0223693 A1 | 7/2019 | Vargas |
| 2019/0223759 A1 | 7/2019 | Page et al. |
| 2019/0231449 A1 | 8/2019 | Diolaiti et al. |
| 2019/0239723 A1 | 8/2019 | Duindam et al. |
| 2019/0239724 A1 | 8/2019 | Averbuch et al. |
| 2019/0239831 A1 | 8/2019 | Chopra |
| 2019/0246876 A1 | 8/2019 | Schaning |
| 2019/0246882 A1 | 8/2019 | Graetzel et al. |
| 2019/0247128 A1 | 8/2019 | Inouye et al. |
| 2019/0250050 A1 | 8/2019 | Sanborn et al. |
| 2019/0254649 A1 | 8/2019 | Walters et al. |
| 2019/0262086 A1 | 8/2019 | Connolly et al. |
| 2019/0269468 A1 | 9/2019 | Hsu et al. |
| 2019/0269470 A1 | 9/2019 | Barbagli et al. |
| 2019/0269885 A1 | 9/2019 | Bailey et al. |
| 2019/0272634 A1 | 9/2019 | Li et al. |
| 2019/0290109 A1 | 9/2019 | Agrawal et al. |
| 2019/0290375 A1 | 9/2019 | Dearden et al. |
| 2019/0298160 A1 | 10/2019 | Ummalaneni et al. |
| 2019/0298451 A1 | 10/2019 | Wong et al. |
| 2019/0298460 A1 | 10/2019 | Al-Jadda et al. |
| 2019/0298465 A1 | 10/2019 | Chin et al. |
| 2019/0320878 A1 | 10/2019 | Duindam et al. |
| 2019/0320937 A1 | 10/2019 | Duindam et al. |
| 2019/0328213 A1 | 10/2019 | Landey et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0350660 A1 | 11/2019 | Moll et al. |
| 2019/0350662 A1 | 11/2019 | Huang et al. |
| 2019/0365199 A1 | 12/2019 | Zhao et al. |
| 2019/0365201 A1 | 12/2019 | Noonan et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0000533 A1 | 1/2020 | Schuh et al. |
| 2020/0000537 A1 | 1/2020 | Marsot et al. |
| 2020/0008655 A1 | 1/2020 | Schlesinger et al. |
| 2020/0008678 A1 | 1/2020 | Barbagli et al. |
| 2020/0008827 A1 | 1/2020 | Dearden et al. |
| 2020/0008874 A1 | 1/2020 | Barbagli et al. |
| 2020/0015901 A1 | 1/2020 | Scheib et al. |
| 2020/0022762 A1 | 1/2020 | Cassell et al. |
| 2020/0022767 A1 | 1/2020 | Hill et al. |
| 2020/0029948 A1 | 1/2020 | Wong et al. |
| 2020/0030044 A1 | 1/2020 | Wang et al. |
| 2020/0030461 A1 | 1/2020 | Sorger |
| 2020/0030575 A1 | 1/2020 | Bogusky et al. |
| 2020/0038123 A1 | 2/2020 | Graetzel et al. |
| 2020/0038750 A1 | 2/2020 | Kojima |
| 2020/0039086 A1 | 2/2020 | Meyer et al. |
| 2020/0043207 A1 | 2/2020 | Lo et al. |
| 2020/0046431 A1 | 2/2020 | Soper et al. |
| 2020/0046434 A1 | 2/2020 | Graetzel et al. |
| 2020/0046436 A1 | 2/2020 | Tzeisler et al. |
| 2020/0054399 A1 | 2/2020 | Duindam et al. |
| 2020/0060516 A1 | 2/2020 | Baez, Jr. |
| 2020/0060771 A1 | 2/2020 | Lo et al. |
| 2020/0069192 A1 | 3/2020 | Sanborn et al. |
| 2020/0069384 A1 | 3/2020 | Fenech et al. |
| 2020/0077870 A1 | 3/2020 | Dicarlo et al. |
| 2020/0077991 A1 | 3/2020 | Gordon et al. |
| 2020/0078095 A1 | 3/2020 | Chopra et al. |
| 2020/0078096 A1 | 3/2020 | Barbagli et al. |
| 2020/0078103 A1 | 3/2020 | Duindam et al. |
| 2020/0078104 A1 | 3/2020 | Bailey et al. |
| 2020/0085514 A1 | 3/2020 | Blumenkranz |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100649 A1 | 4/2020 | Inoue |
| 2020/0100776 A1 | 4/2020 | Blumenkranz et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0107894 A1 | 4/2020 | Wallace et al. |
| 2020/0107899 A1 | 4/2020 | Carlson et al. |
| 2020/0109124 A1 | 4/2020 | Pomper et al. |
| 2020/0121170 A1 | 4/2020 | Gordon et al. |
| 2020/0129045 A1 | 4/2020 | Prisco |
| 2020/0129239 A1 | 4/2020 | Bianchi et al. |
| 2020/0138515 A1 | 5/2020 | Wong |

(56) References Cited

U.S. PATENT DOCUMENTS

| | | |
|---|---|---|
| 2020/0146757 A1 | 5/2020 | Fenech et al. |
| 2020/0155116 A1 | 5/2020 | Donhowe et al. |
| 2020/0163581 A1 | 5/2020 | Kowshik et al. |
| 2020/0163726 A1 | 5/2020 | Tanner et al. |
| 2020/0170623 A1 | 6/2020 | Averbuch |
| 2020/0170720 A1 | 6/2020 | Ummalaneni |
| 2020/0171660 A1 | 6/2020 | Ho et al. |
| 2020/0179058 A1 | 6/2020 | Barbagli et al. |
| 2020/0188033 A1 | 6/2020 | Komp et al. |
| 2020/0188038 A1 | 6/2020 | Donhowe et al. |
| 2020/0197112 A1 | 6/2020 | Chin et al. |
| 2020/0198147 A1 | 6/2020 | Fredrickson et al. |
| 2020/0205903 A1 | 7/2020 | Srinivasan et al. |
| 2020/0205904 A1 | 7/2020 | Chopra |
| 2020/0205908 A1 | 7/2020 | Julian et al. |
| 2020/0206472 A1 | 7/2020 | Ma et al. |
| 2020/0214664 A1 | 7/2020 | Zhao et al. |
| 2020/0217733 A1 | 7/2020 | Lin et al. |
| 2020/0222134 A1 | 7/2020 | Schuh et al. |
| 2020/0222666 A1 | 7/2020 | Chan et al. |
| 2020/0229679 A1 | 7/2020 | Zhao et al. |
| 2020/0237458 A1 | 7/2020 | DeFonzo et al. |
| 2020/0242767 A1 | 7/2020 | Zhao et al. |
| 2020/0253670 A1 | 8/2020 | Doisneau et al. |
| 2020/0254223 A1 | 8/2020 | Duindam et al. |
| 2020/0261172 A1 | 8/2020 | Romo et al. |
| 2020/0261175 A1 | 8/2020 | Fenech |
| 2020/0268240 A1 | 8/2020 | Blumenkranz et al. |
| 2020/0268459 A1 | 8/2020 | Noonan |
| 2020/0268463 A1 | 8/2020 | Au |
| 2020/0275860 A1 | 9/2020 | Duindam |
| 2020/0275984 A1 | 9/2020 | Brisson et al. |
| 2020/0281787 A1 | 9/2020 | Ruiz |
| 2020/0289023 A1 | 9/2020 | Duindam et al. |
| 2020/0297437 A1 | 9/2020 | Schuh et al. |
| 2020/0297442 A1 | 9/2020 | Adebar et al. |
| 2020/0305983 A1 | 10/2020 | Yampolsky et al. |
| 2020/0305989 A1 | 10/2020 | Schuh et al. |
| 2020/0315554 A1 | 10/2020 | Averbuch et al. |
| 2020/0323593 A1 | 10/2020 | Coste-Maniere et al. |
| 2020/0330167 A1 | 10/2020 | Romo et al. |
| 2020/0330795 A1 | 10/2020 | Sawant et al. |
| 2020/0345436 A1 | 11/2020 | Kowshik et al. |
| 2020/0352420 A1 | 11/2020 | Graetzel et al. |
| 2020/0352427 A1 | 11/2020 | Deyanov |
| 2020/0352675 A1 | 11/2020 | Averbuch |
| 2020/0364865 A1 | 11/2020 | Donhowe et al. |
| 2020/0367719 A1 | 11/2020 | Au |
| 2020/0367726 A1 | 11/2020 | Landey et al. |
| 2020/0367981 A1 | 11/2020 | Ho et al. |
| 2020/0375678 A1 | 12/2020 | Wallace et al. |
| 2020/0383750 A1 | 12/2020 | Kemp et al. |
| 2020/0391010 A1 | 12/2020 | Fenech et al. |
| 2020/0405317 A1 | 12/2020 | Wallace |
| 2020/0405411 A1 | 12/2020 | Draper et al. |
| 2020/0405419 A1 | 12/2020 | Mao et al. |
| 2020/0405420 A1 | 12/2020 | Purohit et al. |
| 2020/0405423 A1 | 12/2020 | Schuh |
| 2020/0405424 A1 | 12/2020 | Schuh |
| 2020/0405434 A1 | 12/2020 | Schuh et al. |
| 2020/0406002 A1 | 12/2020 | Romo et al. |
| 2021/0275167 A1 | 9/2021 | Bedoya et al. |
| 2021/0361281 A1 | 11/2021 | O'Shea et al. |
| 2022/0000556 A1 | 1/2022 | Casey et al. |

FOREIGN PATENT DOCUMENTS

| | | | |
|---|---|---|---|
| CN | 101522134 B | * 6/2012 | ......... A61B 17/3478 |
| CZ | 486540 | 9/2016 | |
| CZ | 2486540 | 9/2016 | |
| CZ | 2709512 | 8/2017 | |
| CZ | 3060157 | 12/2019 | |
| CZ | 2884879 | 1/2020 | |
| EP | 3326551 A1 | 5/2018 | |
| EP | 3367915 A4 | 7/2019 | |
| EP | 3413830 A4 | 9/2019 | |
| EP | 3562423 A1 | 11/2019 | |
| EP | 3552653 A3 | 12/2019 | |
| EP | 3576598 A1 | 12/2019 | |
| EP | 3576599 A1 | 12/2019 | |
| EP | 3478161 A4 | 2/2020 | |
| EP | 3641686 A2 | 4/2020 | |
| EP | 3644820 A1 | 5/2020 | |
| EP | 3644885 A1 | 5/2020 | |
| EP | 3644886 A1 | 5/2020 | |
| EP | 3645100 A1 | 5/2020 | |
| EP | 3654870 A2 | 5/2020 | |
| EP | 3668582 A2 | 6/2020 | |
| EP | 3576599 A4 | 11/2020 | |
| JP | 2012120841 | * 6/2012 | ......... A61B 18/1445 |
| JP | 2012120841 A | 6/2012 | |
| MX | 03005028 A | 1/2004 | |
| MX | 225663 B | 1/2005 | |
| MX | 226292 | 2/2005 | |
| MX | 246862 B | 6/2007 | |
| MX | 265247 | 3/2009 | |
| MX | 284569 B | 3/2011 | |
| WO | 2015123699 A1 | 8/2015 | |
| WO | 2019089305 A1 | 5/2019 | |
| WO | WO-2019132781 A1 | * 7/2019 | ......... A61B 17/3403 |
| WO | 2021146339 A1 | 7/2021 | |
| WO | 2021158328 A1 | 8/2021 | |

OTHER PUBLICATIONS

Christoph Staub et all, Automation of Tissue Piercing using Circular Needles and Vision Guidance for Computer Aided Laparoscopic Surgery, May 8, 2010, IEEE Xplore, IEEE International Conference on Robotics and Automation, DOI: 10.1109/ROBOT.2010.5509601 (Year: 2010).*

Cao Lin et al: "A Novel Robotic Suturing System for Flexible Endoscopic Surgery", 2019 International Conference on Robotics and Automation (ICRA), IEEE, May 20, 2019 (May 20, 2019), pp. 1514-1520.

PCT Search Report and Written Opinion issued in PCT/US2021/045827 dated Dec. 1, 2021.

Japanese Office Action issued in Japanese Patent Application No. 2023-507262 dated Feb. 7, 2025 with English Translation.

Notice of Allowance and Issue Fee due issued in related U.S. Appl. No. 17/396,761 dated Nov. 25, 2024.

* cited by examiner

ENDOLUMINAL ROBOTIC (ELR) SYSTEMS AND METHODS

CROSS-REFERENCE TO RELATED APPLICATIONS

This application claims the benefit of the filing date of provisional U.S. Application No. 63/064,938, filed Aug. 13, 2020.

FIELD

The technology is generally related to endoluminal robotic (ELR) systems including subsystems for visualization, navigation, pressure sensing, platform compatibility, and user interfaces, which may be implemented by one or more of a console, haptics, image fusion, voice controls, remote support, and multi-system controls.

BACKGROUND

Medical procedures such as endoscopy (e.g., bronchoscopy) involve accessing and visualizing the inside of a patient's lumen of a luminal network (e.g., airways). During a procedure, an endoscope may be inserted into the patient's body. Another tool or instrument may be passed through the endoscope to target tissue. During such procedures, a physician and/or computer system navigates a medical tool or instrument through the luminal network of a patient in order to diagnose and treat target tissue. Medical robotic systems may be used to insert and/or manipulate the endoscope and the tools or instruments. Robotically-enabled medical systems may be used to perform a variety of medical procedures, including both minimally invasive procedures, such as laparoscopic procedures, and non-invasive procedures, such as endoscopic procedures. Among endoscopic procedures, robotically-enabled medical systems may be used to perform bronchoscopy, ureteroscopy, gastroenterology, etc.

SUMMARY

The techniques of this disclosure generally relate to endoluminal robotic systems and methods.

In one aspect, this disclosure provides an endoluminal robotic system for performing suturing procedures. The endoluminal robotic system includes at least one robotic arm and an endoscopic tool removably coupled to the at least one robotic arm. The endoscopic tool includes an imaging device coupled to the distal end portion of the endoscopic tool. The endoluminal robotic system also includes a needle driver tool removably coupled to the at least one robotic arm and a grasping tool removably coupled to the at least one robotic arm. The endoluminal robotic system also includes a processor and a memory having stored thereon instructions, which, when executed by the processor, cause the processor to: receive an image from the imaging device, overlay a suture needle path on the received image, and control the at least one robotic arm to operate the needle driver tool to drive a suture needle based on the overlaid suture needle path.

The endoluminal robotic system may include a force sensor coupled to the grasping tool. The instructions, when executed by the processor, may cause the processor to determine the force applied to tissue by the grasping tool based on force measurement data output from the force sensor, and generate an alert in response to determining that the force applied to tissue is greater than a predetermined force. The force sensor may include force sensors distributed in an array. The instructions, when executed by the processor, may cause the processor to: determine tissue type based on processing force measurement data output from the force sensor with a machine learning-based algorithm; receive grasping tool type information; and determine the predetermined force based on the tissue type and the grasping tool type information. The instructions, when executed by the processor, may cause the processor to: determine tissue type; acquire grasping tool type information; and set a maximum force applied by the grasping tool based on the tissue type and the grasping tool type.

The suture needle path may include at least one of needle entry marks or needle exit marks. The endoluminal robotic system may include an electromagnetic (EM) field generator configured to generate an EM field and at least one EM sensor coupled to a suture needle. The instructions, when executed by the processor, may cause the processor to track the position of the suture needle based on the EM field sensed by the at least one EM sensor.

The instructions, when executed by the processor, may cause the processor to detect slip of a suture needle and control the at least one robotic arm to operate the endoscopic tool and/or the needle driver tool to account for the detected slip in response to detecting slip of the suture needle. Detecting slip may include detecting movement of the suture needle with respect to the needle driver tool. The instructions, when executed by the processor, may cause the processor to adjust the suture needle path based on a location of the detected slip and overlay the adjusted suture needle path on the received image. Controlling the at least one robotic arm may include controlling the at least one robotic arm to operate the endoscopic tool and the needle driver tool based on the adjusted suture needle path overlaid on the received image.

The endoluminal robotic system may include a user controller. The instructions, when executed by the processor, may cause the processor to provide haptic feedback to the user controller in response to detecting slip of the suture needle. The instructions, when executed by the processor, may cause the processor to generate vibrations in the user controller in response to detecting slip of the suture needle. The endoluminal robotic system may include a pressure sensor. The instructions, when executed by the processor, may cause the processor to generate tissue tension data based on measurement data output from the pressure sensor and predict needle slip based on the tissue tension data.

The instructions, when executed by the processor, may cause the processor to determine a current position and orientation of the suture needle, determine that the suture needle is near tissue, and overlay a mark on the received image showing where the suture needle will exit tissue based on the current position and orientation of the suture needle in response to determining that the suture needle is near tissue. The instructions, when executed by the processor, may cause the processor to overlay a mark on the received image showing a planned location where the suture needle will exit tissue.

The instructions, when executed by the processor, may cause the processor to display critical structures to a side of or behind a suture location on the received image. The instructions, when executed by the processor, may cause the processor to display at least one of an entry location, an orientation, or a depth for the suture needle to avoid approaching critical structures. The instructions, when executed by the processor, may cause the processor to determine an amount of tissue resistance to movement of the suture needle and display the amount of the tissue resistance.

In another aspect, this disclosure provides an endoluminal robotic system. The endoluminal robotic system includes an endoscopic tool, which includes an imaging device coupled to the distal end portion of the endoscopic tool. The endoluminal robotic system also includes a needle driver tool. The endoluminal robotic system also includes a processor and a memory having stored thereon instructions, which, when executed by the processor, cause the processor to: receive an image from the imaging device, overlay a suture needle path on the received image, and control the needle driver tool to drive a suture needle based on the suture needle path overlaid on the received image.

In another aspect, this disclosure provides a method. The method includes receiving an image from a camera disposed on an endoscopic tool, overlaying a suture needle path on the received image, and controlling a robot to operate a needle driver tool to drive a suture needle based on the suture needle path overlaid on the received image. The method also includes detecting slip of the suture needle, adjusting the suture needle path based on the detected slip, and overlaying the adjusted suture needle path on the received image, and controlling the robot to operate the driver tool based on the adjusted suture needle path overlaid on the received image.

BRIEF DESCRIPTION OF DRAWINGS

FIG. 6 is a perspective view of an ELR subsystem for holding tissue in place while it is operated on.

DETAILED DESCRIPTION

For ELR systems, the placement, positioning, and/or structural support of equipment may be challenging. The operating table presents an opportunity to facilitate an ELR procedure through added functionality. The systems and methods of this disclosure may incorporate operating table (OR) table-related enhancements, in which the OR table is part of the robot. For example, robotic arms and instruments, which include tools, may be fixed, and a boom stand may be off of the table. In aspects, the C-arm may be integrated into the OR table. In aspects, the OR table may include swing arms for getting various technology in or out of a working area. This may allow OR staff to be close to the patient if needed during a procedure. Rather than undocking the robotic arms to get access to the patient, the robotic arms can temporarily be positioned out of the way. These features may provide added benefit to surgeons, staff, central processing, and hospitals in that these features may save time, improve process flow, and make working in an OR easier.

Figure 1:
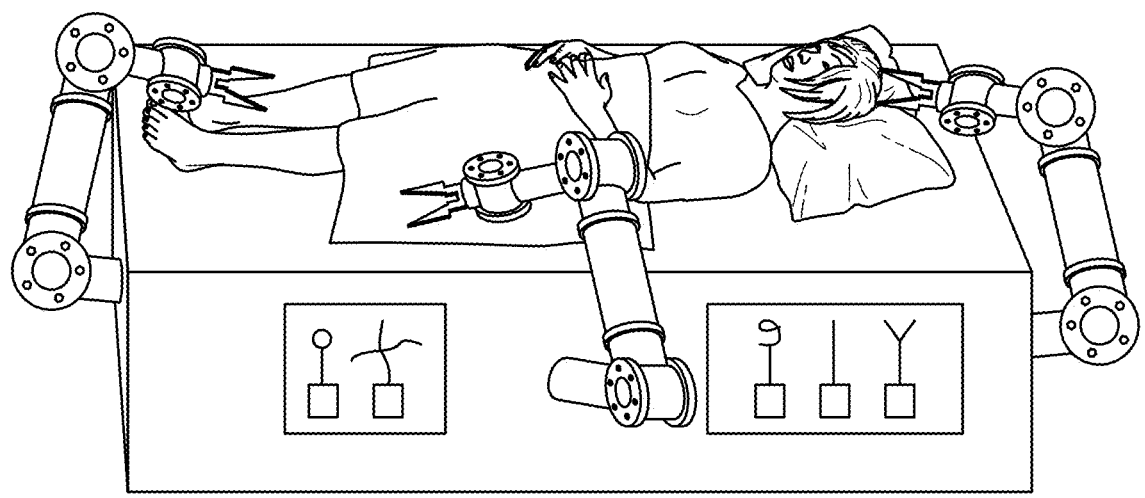
FIG. 1 is a diagram that illustrates an example of an ELR system including a medical tool "shed".

In aspects, the robotic arms and instruments may tuck underneath the table to be out of way, as illustrated in FIG. 1. The robotic arms and instruments may also swing out when needed. The robotic arms and instruments can be stored in this position to free up space in the OR if the robotic arms and instruments are not being used. In aspects, the OR table may include an integrated autoclave or cleaning solution system. Robotic arms and/or instruments can be returned to the "shed" under the table after a procedure and go through an autoclave process or cleaning solution spraying system to clean or sterilize the instruments and/or robotic arms, for example, in a manner similar to a car wash.

In aspects, the OR table may provide for automated attachment of tools in a sterile field. The OR table may include a separate "shed" with tools that may be next to the surgical field (e.g., under the table) where the robotic arms can retreat in order to change instruments. This may be done by stocking certain instruments before a case or procedure and registering their location in the "shed." During the procedure, the surgeon may then select different instruments and the robotic arm may automatically remove an old instrument and attach a new desired instrument.

The systems and method of this disclosure may incorporate automated navigation. The use of careful manual navigation of instrumentation can be time consuming and brings inherent risk to the patient if the surgeon does not make the correct maneuvers. This is especially challenging within the small tubular anatomy through which ELR systems navigate instrumentation. The automated navigation features may allow for easier use of the ELR systems, may provide enhanced functionality that leads to higher safety for patients, or may save OR time.

The ELR systems and methods of this disclosure may provide for automated catheter advancement, braking, or retracement. The ELR systems may store position information in memory for redoing motions. This may be done by storing position and motion information in system memory. This allows for "undo buttons" or retracement back to specific regions that were stored in system memory without having to do manual control.

The ELR systems may use computerized tomography (CT) scans for navigation functionality. The ELR systems may use a CT scan of a patient's anatomy to automate delivery of a tool, therapy, medication, etc. to a specific site of interest.

The ELR systems may provide image stability so that an ELR system may lock onto a target. For example, the ELR systems may compensate for tissue motion or instrument motion.

The ELR systems may provide features relating to the control of instruments that are out of sight or that go out of sight. For example, when an instrument is out of sight or goes out of sight, the ELR system may lock the instrument in place, or, if the instrument is moving, issue an alert when the instrument is not in view.

ELR systems may include improvements to a surgeon console for non-virtual reality (VR) or non-augmented reality (AR) implementations. In aspects, the surgeon console may be located on a swivel, e.g., a 360-degree swivel, that can rotate around the patient depending on the procedure or the location desired by the surgeon or other clinician. The ELR systems may include a head sensor so that screens move automatically relative to the position of the head sensor.

Figure 2:
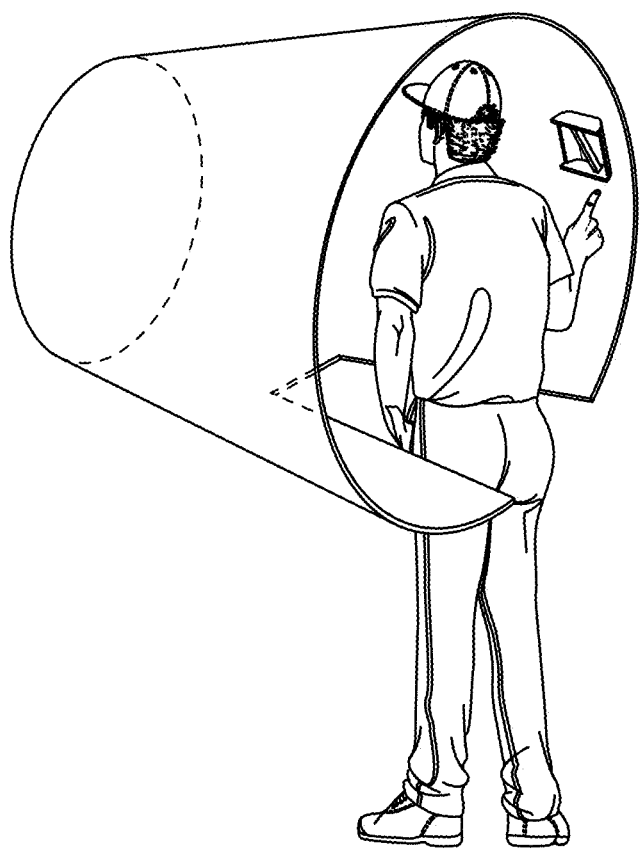
FIG. 2 is a schematic diagram that illustrates a 3D tube in a surgeon console.

The ELR systems and methods may incorporate one or more of a variety of control features. The control features may include mapping an image, e.g., an image of an endoscopic view, onto a physical three-dimensional (3D) tube in the surgeon console to allow the surgeon to touch the surgeon console to control specific locations. Specifically, as illustrated in FIG. 2, the surgeon console may be a 3D tube in which the surgeon stands. Instead of the image being displayed on a 2D screen, the image is mapped on the inside of the 3D tube. The mapping may involve magnifying the image so that the surgeon feels as if the surgeon is physically within the tubular structure in the image. The inner surface of the 3D tube may be a touch screen enabling the surgeon to control the motion of the camera, tools, or virtually marked points of interest on the touch screen. The surgeon may draw virtual boundaries or mark boundaries with energy.

The control features may include a mouse or trackpad for a more intuitive interface. The control features may allow pinch and zoom gestures similar to that found in a conventional laptop, allow left or right clicks to select, and/or provide drop-down menu features. The control features may allow a clinician to move a fiber optic element closer to a target to provide optical zoom functionality, or to crop and enlarge an image to provide digital zoom functionality. The ELR systems may include a trackpad to control features of the ELR system. For example, the trackpad may be used for hand controls.

The ELR systems and methods of this disclosure may use virtual reality (VR) and augmented reality (AR) systems to improve the surgeon console for endoluminal robotic procedures. The ELR systems may include a VR helmet with audio and visual functionality built into the VR helmet with a portable control station. The VR helmet may include a microphone for more intuitive control and more visualization or control options. For example, the clinician wearing the VR helmet may talk into the VR helmet to control one or more features, functions, or subsystems of the ELR systems.

The ELR systems may provide voice-activated actions. The voice-activated actions may include features or functionality provided by Siri, Alexa, or Google home. The ELR systems may provide channels for talking to teammates. The channels may be specific to staff of interest. The voice-activated actions may respond to keywords, e.g., "start" and "stop." Also, the keywords may be specific to certain instruments, e.g., "Alexa, move camera."

The ELR systems may provide body motion detection via, for example, a body suit or specific body part controls. There may be sensor interaction, e.g., a ring on the surgeon's finger needs to be at a specific location to enable access to or use of features of the ELR systems. The speed of motion may add additional controls, e.g., waving an iPhone to delete information.

The VR or AR systems may be used to direct specific image integration or direct which images to show on screens. The VR or AR systems may monitor eye motion for safety or additional commands. The VR or AR systems may monitor eye motion to auto-display options for a given region.

The VR or AR systems may provide directional sounds as alerts. The VR or AR systems may provide tones from different locations to signify different alerts. For example, a high trocar torque alert may be a specific tone coming from behind the clinician. The VR or AR system may provide proximity markers alert based on camera motion or instrument motion.

The VR or AR system may perform surgeon monitoring. For example, the VR or AR system may monitor a surgeon's alertness, heart rate, fatigue, blink rate, or posture and alert the surgeon when needed based on the monitoring. The VR or AR system may monitor and provide features or functions related to ergonomics or posture correction.

Figure 3:
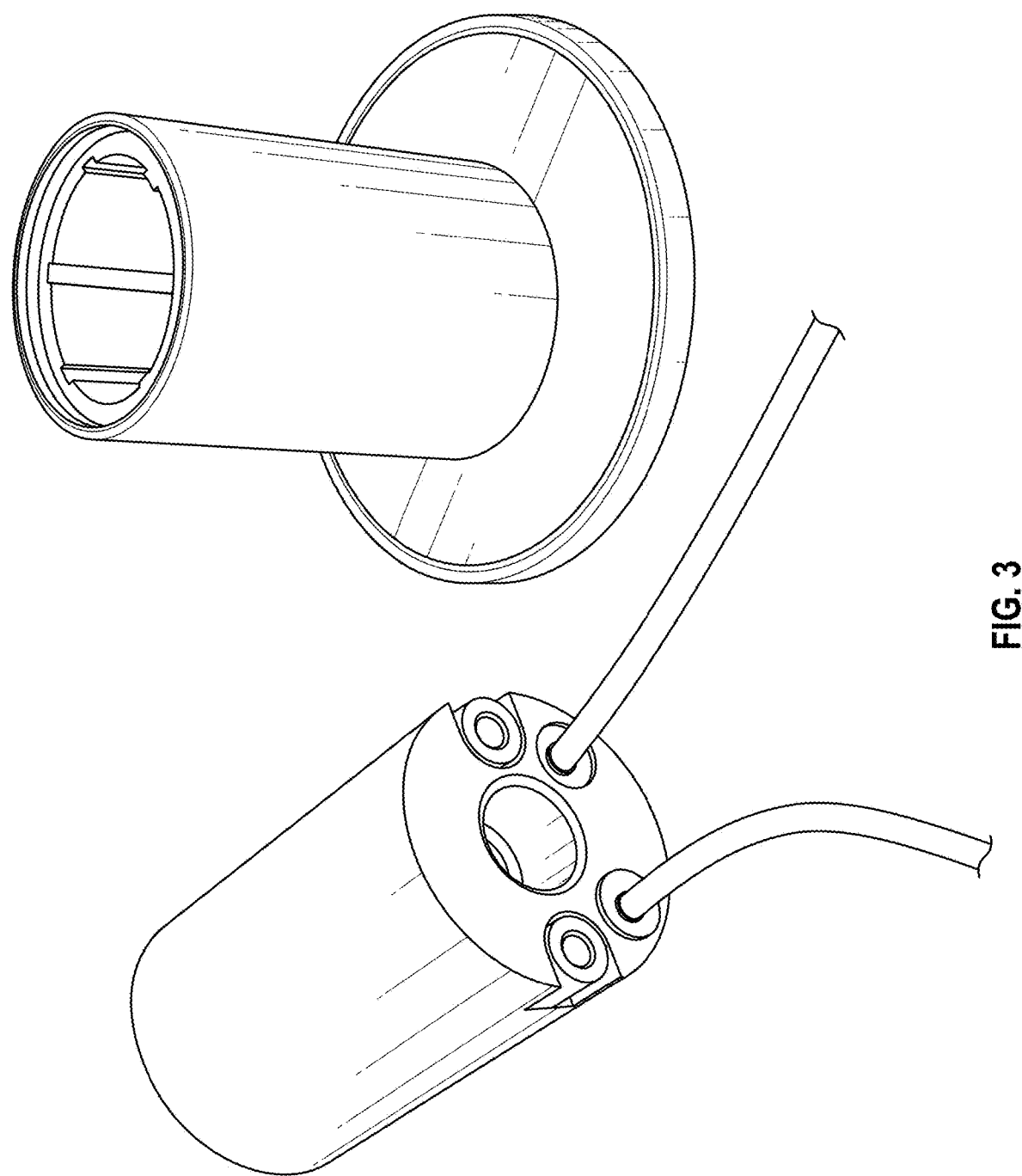
FIG. 3 is a perspective view of a variable focal length camera that illustrates an example of a camera that may be incorporated into ELR systems of the disclosure.

The ELR visualization features may include zoom functionality to improve white light image quality and usefulness. A tubular image may be mapped at a desired magnification (e.g., 10×) for a surgeon to selectively have fine dissection control. The catheter may be moved axially either closer to or farther from the pathology to zoom closer to or have a wider field of view, respectively. The ELR systems may use a lens-less camera system or a variable focal length camera system, which is illustrated in FIG. 3. The camera systems may use ultrasound deformed lenses, which may be made of a soft material.

The ELR systems and methods of this disclosure may incorporate various tissue sensing or haptics features. In aspects, blood perfusion or tissue type may be determined based on oxygen saturation measurements. Motion may be detected using optical or physical sensors (e.g., ureter peristalsis, pulsing of arteries).

The ELR systems and methods may measure compression or tension tissue points. The mobility of compression or tension tissue points show tissue elasticity. Compression or tension of tissue may be measured using pressure sensors or strain gauges. The measured compression or tension of tissue may be used to calculate suture line stress, dilation of stenosis of structures such as the cervix or the bowel, tissue perfusion, or tensile load on tissue while grasping, stapling, or sealing. The measured compression or tension of tissue may be used to calculate grasping force. The ELR systems may transmit an alert to a surgeon when the grasping force is too high. The pressure sensors may be an array of pressure sensors that are circumferentially arranged. Alternatively, a single pressure sensor may be used. Manometry balloons may be used to dilate tissue or a lumen to sense tissue tension and/or movement of tissue such as in peristalsis. The ELR systems may issue vibration alerts to the surgeon when a threshold tissue compression, tension, or movement is crossed.

The ELR systems and methods may include impedance monitoring of tissue (e.g., structure behind the peritoneum, density, or fibrotic tissue scale). The ELR systems may include a lasso, which may include circumferentially-spaced electrodes, to measure tissue impedance along a wall to understand tissue properties, e.g., tissue type, density, fibrotic nature, or the amount of surrounding tissue that is present.

The tissue sensing or haptics features of the ELR systems and methods may be based on force or vibration. The tissue sensing features may include a grasper force sensor to detect the fragility of tissue. Vibrations may alert the surgeon to the strength of a grasp (i.e., soft versus hard for intensity). For example, vibrations may alert the surgeon when the surgeon's grasp is too hard. A clinician may select the tissue type and the ELR system may set a maximum grip strength to use based on the selected tissue type and the instrument type. The ELR system may determine the type of an instrument by reading a radio frequency identification (RFID) tag coupled to the instrument. The ELR systems may use a machine learning-based algorithm to determine tissue type. Alerts or warnings may be set based on the instrument type. Pressure sensors may be disposed along a length of a catheter or integrated into an instrument or camera. Pressure sensors may be used for monitoring dilation, which may drive incremental dilation sizes of the cervix or dilation of stenosis of the bowel. Pressure sensors may be used to determine tensile load when pulling on tissue, e.g., end-to-end colorectal anastomosis (EEA) or ureter re-attachment. Pressure sensors may be used to measure suture line stress.

The ELR systems may initiate a vibration alert based on proximity to an object. A tool or instrument may include a sensor for detecting the sensor's proximity to a location in 3D space. The location in 3D space may be manually marked for future detection of proximity to the location in 3D space. The ELR systems may use distributed pressure sensors, such as a dense array of pressure sensors (e.g., 16 by 32). The distributed pressure sensors may be pressed against tissue for locating hard tissue or pulsatile flow. Image processing or machine learning may be used to detect things.

Figure 4:
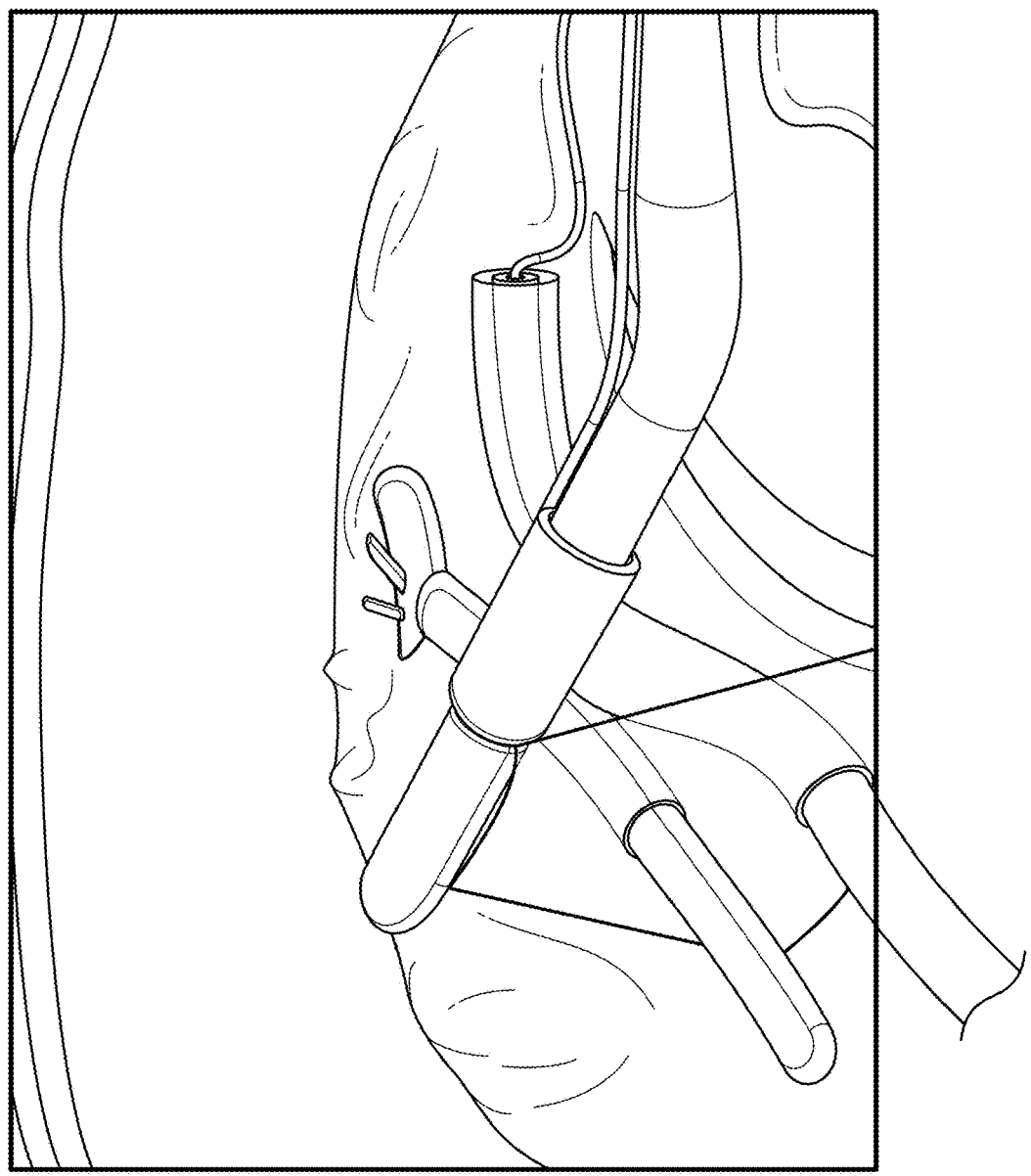
FIG. 4 is a view including multiple images that illustrates a probe for obtaining white light images and a white light image overlaid on an ultrasound image.
Figure 4:
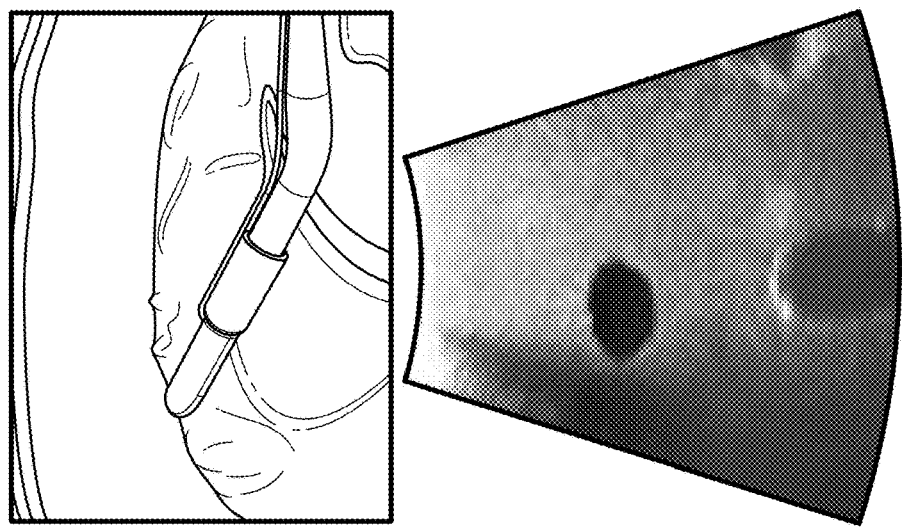

The ELR systems may integrate different imaging modalities to provide useful real-time imaging to assist surgeons. The ELR methods may include performing elastography using ultrasound (US) data, CT data, Mill data, or using a stiffness data probe within the lumen to understand tissue properties along a wall. The ELR systems and methods may display both a white light image and a CT image, for example, by overlaying one image on the other. To improve non-white light image quality or usefulness, near-infrared (NIR) images or ultrasound (US) images may be overlaid or displayed with white light images as illustrated in FIG. 4. This may be extended to pre-operative or peri-operative imaging, including, for example, CT, MRI, US, elastography, X-Ray, laser-encoded, or hyperspectral imaging. The lumen or a balloon within the lumen may be filled with a saline solution, air, contrast, a dye, or any fluid suitable for enhancing the outcome of the imaging modality. Fluid, a saline solution, air and stopper, or balloons may be used to distend tissue in order to improve US visibility inside the lumen. Contrast material or dye, e.g., methylene blue, indocyanine green (ICG), or gas, such as Xenon, may be infused or injected into tissue or fluid inside a cavity.

The ELR systems and methods may use laser encoded or laser spectral imaging for white light imaging as it is smaller and provides high depth of visibility. The ELR systems may include X-ray probes or capsules. For example, an X-ray probe may include a source and a receiver on the tip of the probe and may use reflectance to perform the imaging. The ELR systems may use laser-driven ultrasound (US) without contact and without using the photoacoustic effect. The ELR systems may be configured to perform hyperspectral imaging. The ELR systems may obtain color gradient information from white light imaging and translate the color gradient information into depth perception information in a manner similar to how nurses check for veins before making an intravenous (IV) connection.

Endoluminally suturing may be challenging and may have associated risks. The ELR systems and methods of this disclosure address these potential challenges and risks by projecting a needle path and alerting surgeons when there is a needle slip through haptic feedback. The ELR systems and methods may project a needle path to assist surgeons, for example, with manipulating needles or performing suturing. The needle entry or exit point may be projected to guide surgeons to adjust as tissue moves during a procedure, for instance, when tissue is grasped. For example, when suturing, the needle projection can direct the position of the needle to a desired location. Electromagnetic (EM) tracking may be used to track the needle in real-time in a manner similar to catheter navigation.

In aspects, the ELR systems and methods may account for needle slip in real-time and may adjust the needle trajectory accordingly. The location and orientation of the needle in the driver tool determines where the needle will pass through the patient anatomy. A poorly aimed suture needle may not produce effective sutures and may pass through a critical structure or snare objects into the suture that should not be snared, possibly causing future patient complications. The ELR methods of this disclosure may include 3D imaging of the suture needle and driver tool, which simplifies and/or provides an additional method for slip detection. Optical detection of needle slippage may be performed using one or more imaging devices, e.g., white light cameras, and image processing software. The goal of the image processing software is to detect independent motion of the suture needle or the driver tool. The suture needle and driver tool are expected to move as one unit when no slippage occurs. Additionally, the suture needle and driver tool should move with the same angular motion. Using an image processing software with object identification, such as a convolutional neural network (CNN), the driver tool and the suture needle can be detected in each frame of video. Points on the tool and the needle are selected for motion measurement. When no slippage is occurring, all points should move with the same direction and velocity.

Provision of additional cameras allows an increase in detail and detection of slippage. Tissue tension data, which may be obtained through imaging, machine learning or other suitable tissue sensing techniques, may be used to predict, alert, and/or compensate for needle slip. The ELR system may provide haptic feedback, e.g., resistance, in response to detected needle slip, to guide the surgeon to the desired path, but still allow the surgeon to have control. The ELR system may provide vibrations when needle slip is detected.

Figure 5A:
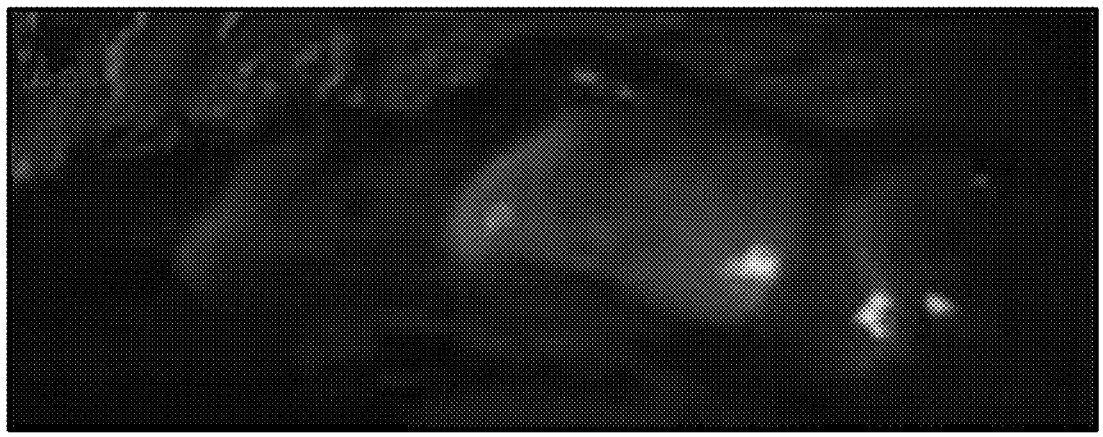
FIGS. 5A-5C are multiple images that illustrate near-infrared (NIR) imaging with an indocyanine green (ICG) marker.
Figure 5B:
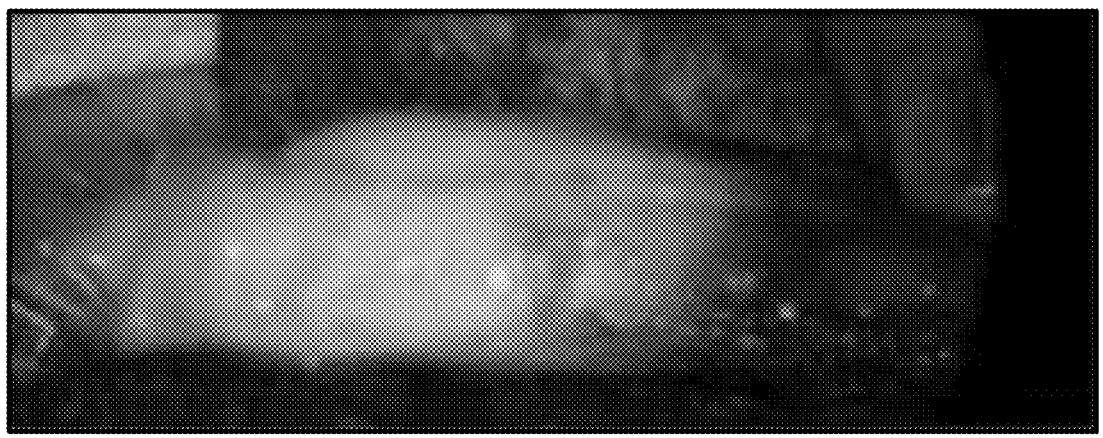
Figure 5C:

Visualization and tracking in endoluminal procedures may be a challenge. The ELR systems and methods of this disclosure may use indocyanine green (ICG) for high-definition imaging to improve visualization and tracking. According to aspects of this disclosure, Near-Infrared (NIR) imaging with markers such as ICG (as illustrated in FIGS. 5A-5C) or cancer detection markers, such as Surgilab markers, along with white-light imaging may be used to guide ELR procedures. Electromagnetic tracking may also be used to better guide endoluminal procedures. The ELR systems and methods of this disclosure may use NIR imaging along with white light imaging in ELR to: track the direction of blood flow, combine laparoscopic and endoluminal tracking of ELR catheters, perform chip-based NIR for cancer detection using markers such as the Surgilab molecule (TR).

The ELR systems and methods of this disclosure may incorporate ELR catheter navigation including electromagnetic (EM) tracking and retraction. The catheter navigation may include 3D tracking of instruments relative to certain point (e.g., tracker on the catheter). The ELR catheter or instrument tip path may be tracked using electromagnetic sensing. The electromagnetic sensing may be performed by a subsystem that uses a drape or sheet with transmitters at different locations and a receiver or sensor disposed at the tip of the ELR catheter or instrument. Based on a signal received by the sensor, the tip of the ELR catheter or instrument may be tracked as a function of the patient's bed.

Using the information about the path and optionally using pre-operative or peri-operative imaging with or without machine learning, the ELR system may predict and automate driving catheter forward or retracting the ELR catheter or instrument back. The ELR controls may be similar to a gas pedal, brake pedal, or reverse gear features in a typical car.

Anatomical parts may be marked with temporary metal clips for tracking functions, e.g., for tracking a catheter in a ureter. Specific distances or margins may be detected by suitable sensors. The ELR system may issue an alarm when a robotic arm or instrument is within proximity of the markers, which may be associated with critical structures.

The ELR systems and methods of this disclosure may use transient images or video to reconstruct a 3D image or model of anatomy. Imaging from one or more imaging modalities may be used to reconstruct 3D anatomy and track the ELR catheter or instrument for helping surgeons visualize real-time navigation. Virtual colonoscopy or bronchoscopy images may be taken and computer vision may be used to reconstruct a 3D model of the anatomy, e.g., an organ. The reconstructed 3D model may be fit with what the clinician sees in the camera. The reconstructed 3D model may be updated as the procedure is progressing. In aspects, CT or fluoroscopic imaging may be used for 3D reconstruction to see where the ELR catheter, tool, or instrument is located and/or as an overlay for real-time guidance.

The ELR systems and methods may use multiple cameras views that are stitched together to give a wider variety of views.

The ELR systems and methods of this disclosure may incorporate visualization features and functions various types of cameras at various locations to improve white light image quality or usefulness. Cameras may be placed on the front tip, the side, and/or facing the back of the face of the ELR catheter or instrument to capture more views. The views may be reconstructed to get a better field of view or to get a 3D map with depth perception. Cameras may be attached on the catheter or instrument tip. The cameras may pop-up or be located on the side of the catheter or instrument. The cameras may be implemented by a chip-on-tip, which may incorporate near infrared (NIR) imaging capabilities; a fiber optic component, or any other lens system suitable for placement on the catheter or instrument tip. Micro-Electro-Mechanical Systems (MEMS) technology may be used to build multiple lenses into the ELR system that can be turned on or off to get different fields of view.

The ELR system may include a capsule endoscopy device, e.g., a PillCam, which looks forward and backward using a front camera and a rear camera, respectively. The two cameras may provide proximal and distal views of the pathology. This may be used for retrograde resection of the pathology. Alternatively, a front-facing camera and a back-facing camera may be coupled to the endoscope or the catheter to obtain images including forward and backward views. Images including the two camera views may be obtained during a preoperative endoluminal survey. Then, images including the two camera views may be obtained at a later time (e.g., intraoperatively) and compared to the images including the two camera views of the preoperative endoluminal survey. In one aspect, the images of the two intraoperative camera views may be overlaid on the two preoperative camera views, respectively, and displayed to a user on a display.

In aspects, a 3D model may be reconstructed using images from the capsule endoscopy device. Landmarks may be identified and frame-by-frame stitching may be performed. The stitching may include stitching progressive views captured by an optical sensor together into a continuous view of the anatomy as the capsule endoscopy device passes by.

Magnets may be placed outside a patient's body to fix cameras or LEDs along an anatomical wall, e.g., the abdominal wall, during procedures. The LEDs may have different wavelengths to provide differentiated visibility.

The cameras may provide an orthogonal side view with articulation. In aspects, a wider field of view may be mapped with two imaging devices, e.g., cameras, coupled to the endoscope. For example, one of the imaging devices may be coupled to the side of the endoscope. A 2D view, a 3D view, or some other adaptation may be presented. The ELR systems and methods may include a Google street view-like feature.

The ELR systems may include different catheters. The different catheters may include a catheter for white light and a catheter for a camera. A camera may be placed on each instrument, e.g., in a multi-articulated system. Structure of light, time of flight, and stereoscopic views may be used for 3D mapping.

The ELR system may incorporate endomicroscopy. This may be used for biopsy. For example, all or a portion of an endomicroscope may be inserted or otherwise incorporated into the biopsy needle.

The ELR system may include multiple cameras splitting a common fiber optic channel connecting to different sensors at the distal end portion.

In aspects, suction may be used to pull tissue or provide tissue tension. The suction may suck tissue into the ELR system to isolate the tissue or organ of interest. This feature may be used in conjunction with endomicroscopy. The ELR system may include a suction channel, which sucks tissue into a tip before using other arms (in a multi-arm articulated ELR system for large bore applications) to perform tasks, such as suturing.

The ELR systems and methods of this disclosure may stabilize cameras, visibility, and/or instruments using, for example, air pressure or insufflation. Localized pressure may provide for easier advancement of a catheter through a lumen. The ELR systems may include a balloon catheter, which uses balloons for locomotion or articulation of the catheter. A proximal balloon and a distal balloon may be used to stretch out the area of tissue. The ELR systems and methods may insufflate between the proximal and distal balloons to open up a lumen.

The distal tip of the catheter may not necessarily be used to provide stabilization. One or more instruments may come out of the side of the catheter at a more proximal location and, in this configuration, may provide stabilization. Balloons proximal and/or distal to the catheter or instrument opening may be used to provide stabilization. The ELR systems and methods may provide image stabilization functionality. Vibrations of the ELR catheter or instrument tip may be sensed by piezo sensors or by image movement detection. Image movements may be compensated for by adding mechanical damper to the ELR catheter or instrument tip or by video processing such as smoothing. The ELR systems may provide the ability to lock cameras or instruments at a desired location. This may be especially applicable to catheters or instruments that are out of view. The ELR systems may issue an alert to the surgeon if the cameras or instruments are forced to move.

Figure 6:
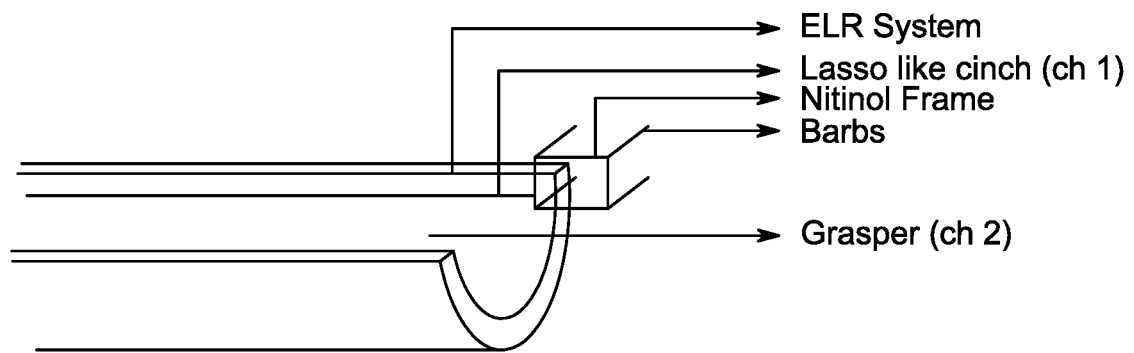

The ELR systems may include a Nitinol (or other memory active materials that can change properties based on Electromagnetic or thermal fields) frame with barbed-like fixation (e.g., a barbed stent-like fixation) to come out of the working channel to hold tissue in tension while it is resected or operated on, as illustrated in FIG. 6. The ELR systems may include a stiffening endoscope, which may be implemented by a pully wire system to pull components together. The stiffening endoscope may use material that changes with different electric or thermal fields (e.g., memory-active materials that change in the presence of magnetic, electric, or thermal fields). The stiffening endoscope may use a garden hose-like design that stiffens when filled with a fluid, e.g., a saline solution. An ELR channel may be filled once the endoscope reaches target anatomy so that the endoscope can stiffen up to provide better stabilization. The endoscope may retract when the fluid leaves the ELR channel. The ELR systems and methods may use magnets outside the body to stabilize and/or drive the distal tip of an ELR catheter or instrument. The ELR systems may include a rolling sleeve to open up or advance along a lumen (similar to water tube toys, snakes, or water wigglies) to roll up to drive the catheter forward. This may also provide stabilization.

The ELR systems and methods may include manometry or a balloon catheter. A balloon catheter with saline may be used to get a pressure mapping. Manometry may be used to detect peristalsis. When peristalsis is detected, the procedure may be paused until a wave has passed. Manometry may be used to detect stricture or dilation. A balloon catheter may be used to open up a lumen. Manometry may be used to check for suture line defects. Manometry may be performed along the length of the endoscope. This may be used to help with navigation.

The ELR systems and methods of the disclosure may provide for platform compatibility. The ELR systems may integrate with robotic-assisted surgery (RAS) systems. The ELR systems may use RAS system design and components except for a single port (multi-arm multi-articulated) system that goes in the place of a trocar holder.

In aspects, the ELR systems and methods may be used in a Combined Endoscopic Laparoscopic Surgery (CELS) application. The combined endoluminal robotic approach allows for the use of an endoluminal and general surgery robot. Tracking where all instruments are located using both ELR and RAS systems may lead to key surgical steps.

The combined ELR and RAS system may allow for switching between laparoscopic and endoscopic views. In other words, the combined ELR and RAS approach may allow for switching views between ELR and RAS. The views could be changed both manually, e.g., via a toggle switch at a common surgeon console, or automatically, e.g., via tracking the stage in the procedure and automatically changing the view based on the stage in the procedure. For example, the combined system may switch between ELR and RAS views during a suturing procedure. In one implementation, while doing inside to outside suturing, the needle tip may be tracked and the system may automatically switch views based on the position of the needle tip, e.g., based on whether the needle tip is inside or outside. In aspects, whenever ELR and RAS tools need to interact, e.g., while performing full thickness suturing or applying tension to tissue, the tools may be tracked to perform this functionality.

The coordination of tools during a CELS procedure may involve the following features. During CELS, for example, a team of surgeons may coordinate use of laparoscopic instruments used in visually-aided, minimally-invasive surgery with endoluminal tools for polyp and cancer resection. The combination of the tools allows the surgical team to better identify the location of the surgical site while providing alternate options for preceding with the procedure based on what is learned in surveying the surgical site. For example, a surgeon may recognize that a polyp is not removable via a colonoscope due to local anatomy such that a laparoscope is required to complete the procedure.

This disclosure describes methods to recognize and relay the positional orientation between endoscopic and laparoscopic tools in real-time. Electro-navigation is a method used to tracking devices in the body and is common practice for Electro-Navigation Bronchoscopy (ENB). The bronchoscope or biopsy tools can have an electromagnetic sensor attached to the distal tip while the patient lays on an electromagnetic field generator. Detection of distortions in the field correlate to a position of the sensor in 3D space. By placing such sensors on each tool used in the CELS procedure, one may track the positional orientation of each tool. With a reference sensor placed in a known anatomic location or using a calibration procedure based on known anatomic structures, the 3D positions may be referenced and overlayed on the patient's CT or fluoroscopic image to show relation to anatomy.

An alternative to electro-navigation is use of radio signals. In this embodiment, the sensor board is replaced with a phase array antenna and each surgical device sensor is replaced with a low power transmitter. Each device generates a uniquely coded signal that is specially located by measurement of phase and angle by the antenna array. The transmitter may be split axially such that two halves of the instrument distal tip produce opposite phase signals to allow recognition of rotational orientation. An additional transmitter further proximal on the instrument would afford recognition of instrument angle.

Another aspect is placement of an infrared (IR) laser source in the endoluminal distal tip projecting out axial to the body of the endoluminal catheter. With the catheter distal tip pointed at the desired surgical site, IR penetration through the colon would be sufficient to allow detection of the IR light on the abdominal side of the colon wall, allowing a laparoscopic tool with IR detection to identify the IR source and 'home in' on the location. This provides the surgeon with directional information in locating the intended surgical site. Using the diffusion pattern of the IR light in the colon wall would allow the laparoscopic tool to identify the brightest location, correlating to the center of the IR beam.

Additionally, using a method to detect orientation of the distal tip of the endoluminal catheter in relation to the patient may inform the surgeon as to the location of the surgical site in relation to the patient (e.g., it is supine or prone, left or right). Methods to detect orientation of the distal tip of the endoluminal catheter include using two electromagnetic sensors spaced sufficiently apart to provide distinct 3D coordinates, or using an inertial measurement unit to detect distal tip orientation in relation to gravity. If laparoscopic tool rotation and angle information is available, the one or more tools may be presented in the view with navigation cues.

Figure 7:
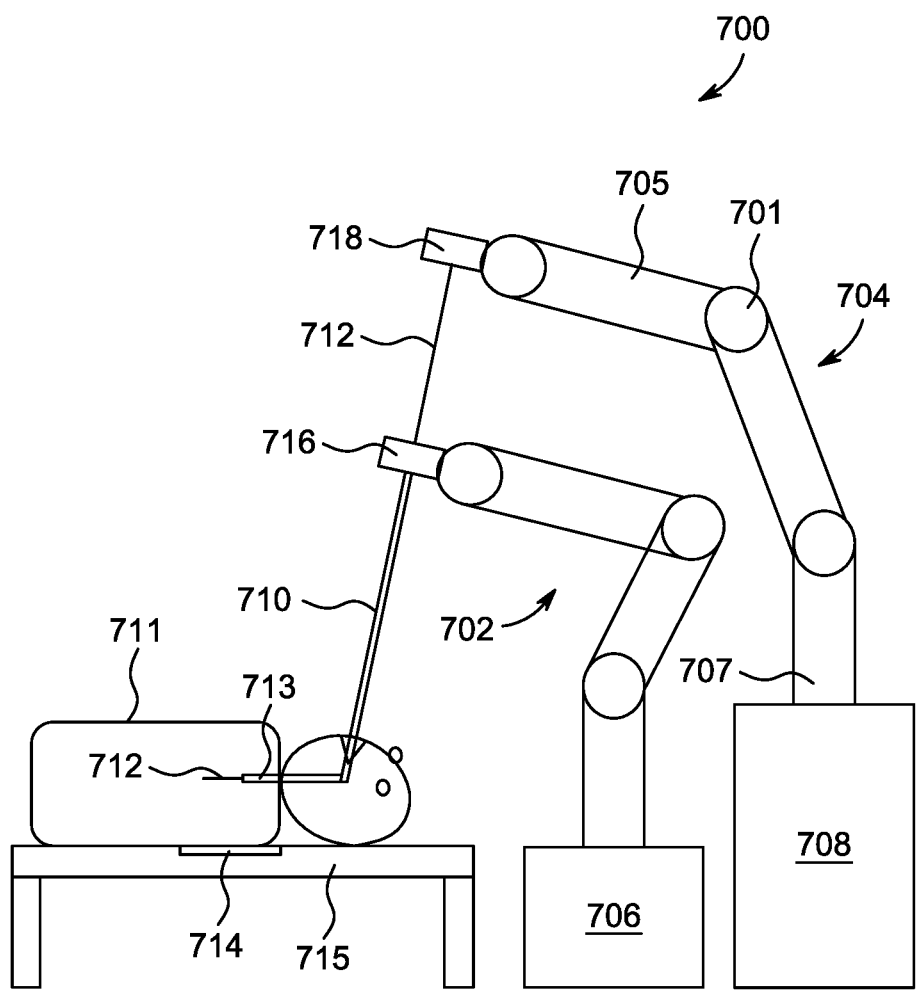
FIG. 7 is a block diagram that illustrates a robotic surgical system.

FIG. 7 is a block diagram that illustrates a robotic surgical system 700 in accordance with aspects of this disclosure. The robotic surgical system 700 includes a first robotic arm 702 and a second robotic arm 704 attached to robotic arm bases 706 and 708, respectively. The first robotic arm 702 and the second robotic arm 704 include a first end effector 716 and a second end effector 718, respectively. The end effectors 716, 718 may include robotic manipulators or grippers suitable for operating the endoscopic catheters and tools of this disclosure. The first end effector 716 operates one or more tools 712, including a suture needle driver tool, a grasping tool, and/or a flexible endoscope (not shown). The second end effector 718 operates a sheath or catheter 710, which may include one or more channels for receiving and guiding the one or more tools 712. The robotic surgical system 700 may further include an electromagnetic (EM)

generator 714, which is configured to generate an EM field, which is sensed by an EM sensor incorporated into or disposed on the suture needle. Additionally, or alternatively, the EM sensor may be incorporated into or disposed on a distal end portion of the driver tool. The EM sensor may output sensor measurement data, which may be used to determine the position and orientation of the suture needle. In aspects, the EM generator 714 may be embedded in the operating table 715 or may be incorporated into a pad that may be placed between the operating table 715 and the patient 711.

The first and second robotic arms 702, 704 may be controlled to align the end effectors 716 and 718 such that proximal end portion of the catheter 710 is distal to the proximal end portions of the one or more tools 712, and such that the one or more tools 712 remain axially aligned with catheter 710.

In one aspect, the first robotic arm 702 inserts the catheter 710 through, for example, a tracheal tube (not shown) in the mouth of the patient 711, and into the bronchial system of the patient 711. Then, the second robotic arm 704 inserts the one or more tools 712 through the catheter 110 to reach a target within the bronchial system of the patient 711. The first and second robotic arms 702, 704 may move the catheter 710 and one or more tools 712 axially relative to each other and into or out of the patient 711 under the control of a surgeon (not shown) at a control console (not shown).

A navigation phase may include advancing catheter 710 along with the one or more tools 712 into the patient 711, and then advancing the one or more tools 712 beyond the distal end of the catheter 710 to reach a desired destination such as a target. Other modes of navigation may be used, such as by using a guide wire through a working channel of the catheter 710. The surgeon may use a visual guidance modality or a combination of visual guidance modalities to aid in navigation and performing the suturing procedures, such as fluoroscopy, video, computed tomography (CT), or magnetic resonance imaging (MM). In aspects, the one or more tools 712 are deployed through longitudinally-aligned working channels within the catheter 710 to perform a suturing procedure and any other desired procedures. In aspects, the robotic arms 702, 704 include three joints 701 and three arm segments 705. In other aspect, the robotic arms 702, 704 may include greater than or less than three joints 701 and three arm segments 705.

Figure 8:
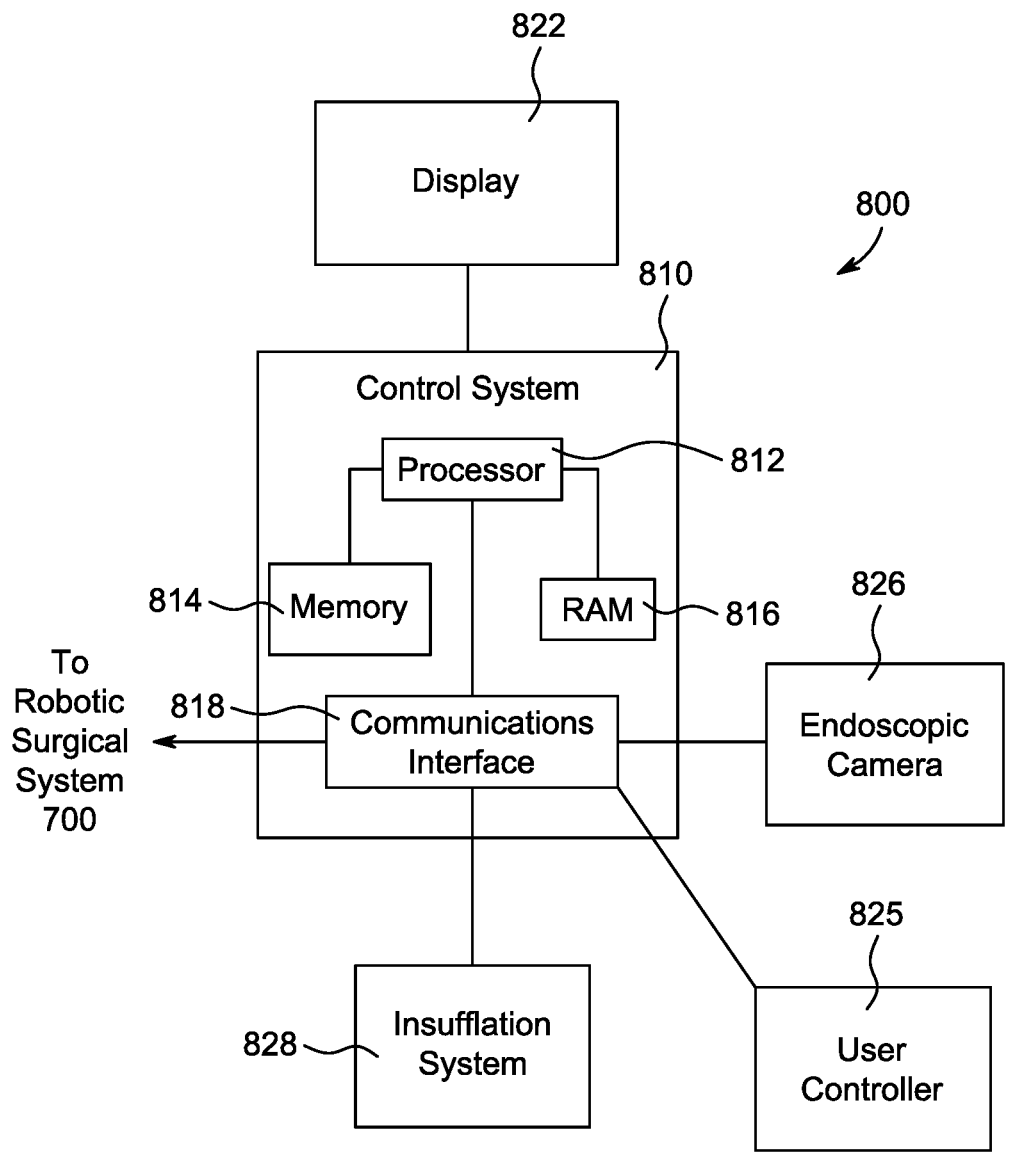
FIG. 8 is a system block diagram that illustrates a robotic surgical control system for controlling the robotic surgical system of FIG. 7.

FIG. 8 is a block diagram that illustrates a robotic control system 800 for controlling the robotic surgical system 700 of FIG. 7. The robotic control system 800 includes a control system 810, which controls the robotic surgical system 700. For example, the control system 810 may execute the method 1000 of FIG. 10. The control system 810 may interface with a display 822, a user controller 825, an endoscopic camera 826, and an insufflation system 828. The control system 810 may be coupled to the robotic surgical system 700, directly or indirectly, e.g., by wireless communication. The control system 810 includes a processor 812, a memory 814 coupled to the processor 812, a random access memory (RAM) 816 coupled to the processor 812, and a communications interface 818 coupled to the processor 812. The processor 812 may include one or more hardware processors. The control system 810 may be a stationary computing device, such as a personal computer, or a portable computing device such as a tablet computer. Alternatively, the control system 810 may be incorporated into one of the robotic arm bases 706, 708. The control system 810 may also interface with a user controller 825, which may be used by a surgeon to control the robotic arm system 824 to perform a suturing procedure.

It should be appreciated by those skilled in the art that the memory 814 may be any computer-readable storage media that can be accessed by the processor 812. That is, computer readable storage media may include non-transitory, volatile, and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray, or other optical storage, magnetic cassettes, magnetic tape, magnetic disk storage or other magnetic storage devices, or any other medium which may be used to store the desired information, and which may be accessed by processor 812.

An application stored in the memory 814 may, when executed by processor 812, cause display 822 to present a user interface (not shown). The user interface may be configured to present to the user endoscopic images from the endoscopic camera 826. User interface may be further configured to direct the user to select the target by, among other things, identifying and marking the target in the displayed fluoroscopic 3D reconstruction or any other fluoroscopic image data in accordance with this disclosure.

Communications interface 818 may be configured to connect to a network such as a local area network (LAN) consisting of a wired network and/or a wireless network, a wide area network (WAN), a wireless mobile network, a Bluetooth network, and/or the internet. Communications interface 818 may be used to connect between the control system 810 and the endoscopic camera 826. Communications interface 818 may be also used to receive image data from the memory 814 and suture path planning data. The control system 810 may also include an input device (not shown), which may be any device through which a user may interact with the control system 810, such as, for example, a mouse, keyboard, foot pedal, touch screen, and/or voice interface. The control system 810 may also include an output module (not shown), which may include any connectivity port or bus, such as, for example, parallel ports, serial ports, universal serial busses (USB), or any other similar connectivity port known to those skilled in the art.

Figure 9:
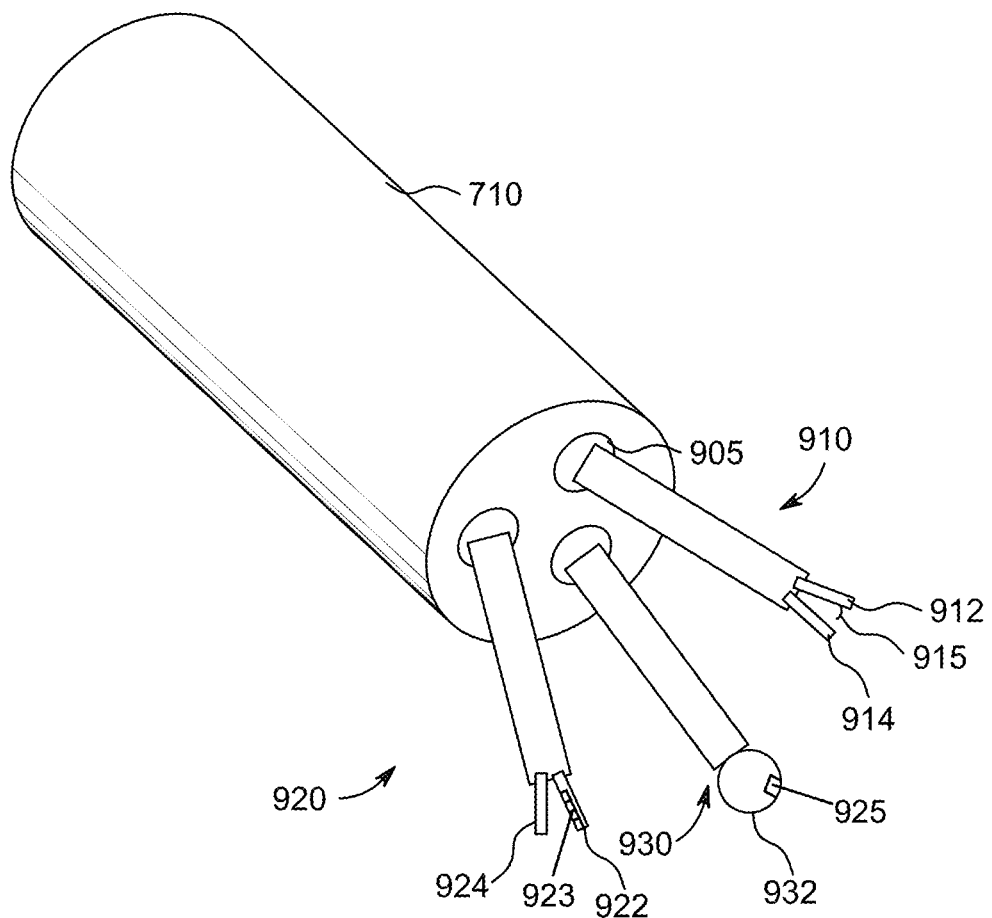
FIG. 9 is a perspective view of a distal portion of a catheter assembly for use with the robotic surgical system of FIG. 7.

FIG. 9 is a perspective view of a distal portion of the catheter 710 of FIG. 7 with various tools disposed therein. The catheter 710 includes working channels 905 in which a suture needle driver tool 910, a grasping tool 920, and an endoscope 930 may be disposed. The suture needle driver tool 910 includes jaw members 912, 914, which may be controlled by the robot end effector 718 of FIG. 7 to transfer a suture needle 915 back and forth between the jaw members 912, 914. The grasping tool 920 includes jaw members 922, 924, which may be used together with the suture needle 915 to perform a suturing procedure, e.g., to tie a knot after the suture thread has been placed. A force sensor 923, which may include force sensors distributed in an array, may be coupled to the grasping tool 920. The endoscope 930 includes a camera 932, which may be used to capture video images of the operation site. A pressure sensor 925 may be integrated into the camera 932. The endoscope 930 may be a monocular endoscope, a stereoscopic endoscope, a 3D endoscope, or any other suitable endoscopic camera for capturing clear video images of a defect to be sutured and surrounding tissue. One or more of the captured video images may be fused with other information to guide the surgeon and/or the robotic surgical system in operating the driver tool 910 and the grasping tool 920 to perform a suturing procedure. A planned needle trajectory, suture needle entry points, and/or critical structures to avoid may be overlayed on the captured video images.

Figure 10:
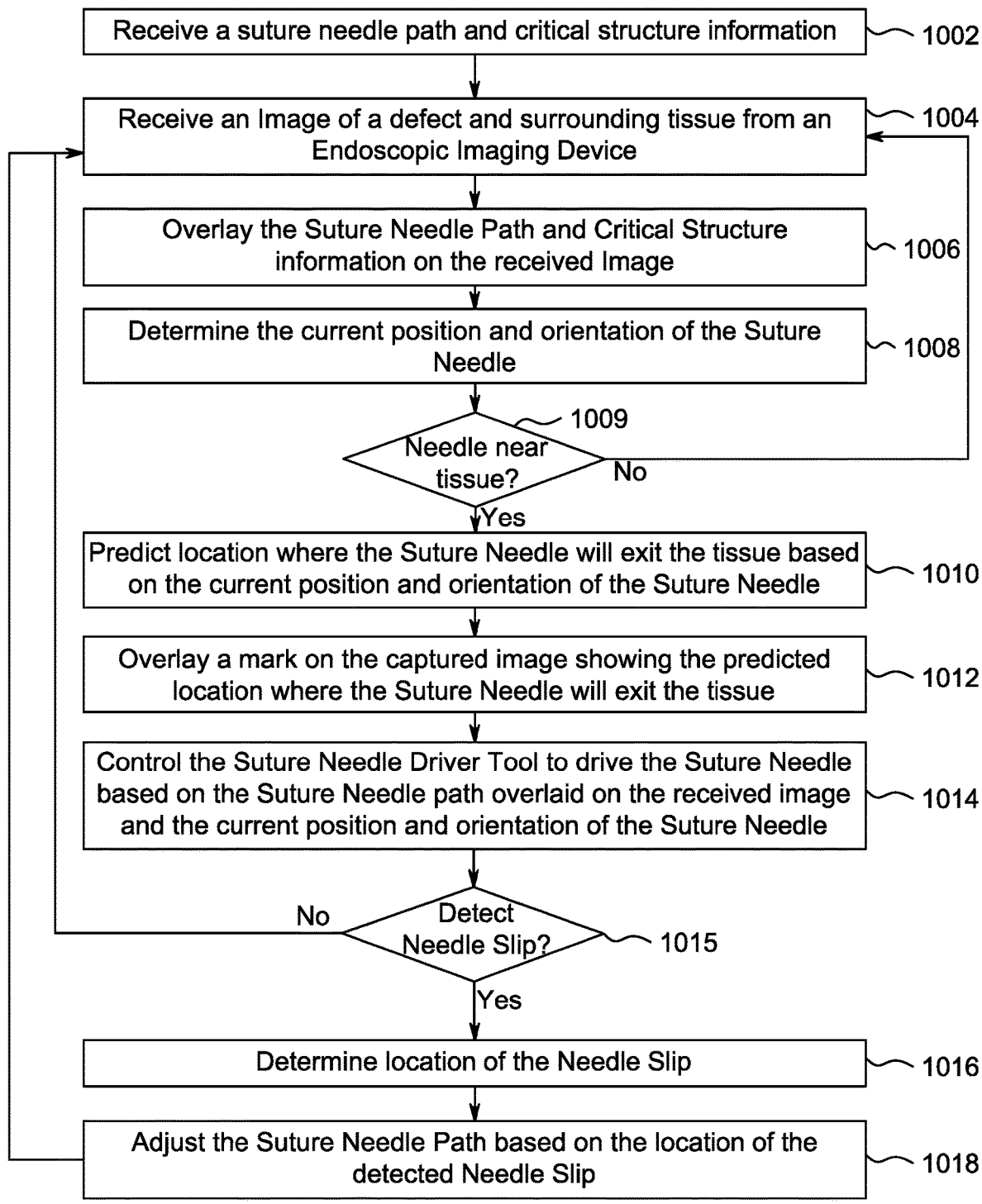
FIG. 10 is a flow diagram that illustrates a method of performing an endoluminal robotic suturing procedure.

FIG. 10 is a flow diagram that illustrates another method of performing a robotic suturing procedure. At block 1002, a suture needle path and critical structure information is received. The critical structure information may include or be derived from three-dimensional pre-operative images. The suture needle path may be generated in a path planning application in which a surgeon can mark entry and exit points on a two-dimensional or three-dimensional image showing a defect to be sutured that is presented to the surgeon in a suitable user interface. Alternatively, the user interface may allow the user to select the suture pitch or spacing and the length of the suture line. At block 1004, an image of a defect and surrounding tissue is received from an endoscopic imaging device. In aspects, the camera sensor may be disposed on the driver tool or the grasping tool. At block 1006, the suture needle path and critical structure information is overlaid on the received image. The suture needle path or trajectory may include at least one of needle entry marks or needle exit marks.

In aspects, the suture needle path may be received from a planning user interface, which may display an image or representation of a defect and allow a surgeon to draw and/or mark a suture needle path on the image or representation of the defect. In some aspects, at least a portion of the suture needle path may be automatically generated. Automatically generating the suture needle path may include determining dimensions of a defect to be sutured based on imaging of the defect (e.g., images received from an endoscopic camera), receiving parameters for a suture pattern, and generating a suture needle path based on the determined dimensions of the defect and the received parameters. The parameters for the suture pattern may include a distance between suture loops.

The critical structure information may include graphical representations of critical structures in the vicinity of or near the defect to be sutured. The received image may be displayed in a user interface. For example, a representation of a vessel and a representation of an organ may be displayed. The graphical representations of the critical structures may be displayed in such a way that the defect in the tubular anatomical structure (e.g., the upper or lower gastrointestinal (GI) tract), the entry marks, the suture needle path, and the representation of the suture needle are visible to the surgeon or other clinician. For example, the graphical representations of the critical structures may be displayed such that they are semi-transparent or ghosted out. In some aspects, the control system may enter a novice mode, which prevents further movement of a robotic arm, if the distance to a critical structure is less than a predetermined distance. And the system may provide a way to manually override the novice mode, such as actuating a physical button or switch.

At block 1008, the current position and orientation of the suture needle is determined. The current position and orientation of the suture needle may be determined based on an electromagnetic (EM) field sensed by the at least one EM sensor incorporated into or disposed on the suture needle or the driver tool. If the at least one EM sensor is incorporated into or disposed on the driver tool, the position and orientation of the suture needle may be determined by controlling the driver tool to hold the suture needle at a predetermined position and in a predetermined orientation relative to the driver tool and calculating the position and orientation of the suture needle based on the position and orientation information from the EM sensor and the predetermined geometrical relationship between the driver tool and the suture needle. Alternatively, the current position and orientation of the suture needle may be determined based on the 3D endoscopic images or ultrasound images. AI algorithms, such as image recognition algorithms, may be employed to determine the current position and orientation of the suture needle. The AI algorithm may include a prediction algorithm to predict a future position and orientation of the suture needle based on the previous and current 3D endoscopic images or ultrasound images. The future position and orientation information may be used to determine and display a where the suture needle will exit the tissue after passing through the tissue.

At block 1009, the method 1000 determines whether the suture needle is near tissue. If the suture needle is determined not to be near the tissue, blocks 1004-1008 are repeated. If the suture needle is determined to be near tissue, the location where the suture needle will exit the tissue is predicted based on the current position and orientation of the suture needle at block 1010. At block 1012, the predicted location of the exit mark is overlayed on the received endoscopic image showing where the suture needle will exit the tissue based on the current position and orientation of the suture needle.

At block 1014, at least one robotic arm is controlled to operate the suture needle driver tool to drive the suture needle based on the suture needle path overlaid on the received image and the current position and orientation of the suture needle. In aspects, the at least one robotic arm may include a robotic end effector coupled to the suture needle driver tool.

At block 1015, the method 1000 determines whether suture needle slip is detected. The suture needle slip may be detected by detecting movement of the suture needle with respect to the suture needle driver tool or a jaw member of the suture needle driver tool currently holding the suture needle. In aspects, suture needle slip may be detected or predicted and then compensated for using tissue tension data, which may be obtained from imaging, machine learning, manometry balloons, which dilate tissue to measure tension, pressure sensor, and/or strain gauge. The pressure sensor or strain gauge may include a singular sensor incorporated into or disposed on a probe or catheter, or an array of sensors that are circumferentially arranged around a probe or catheter. The pressure sensor may also be used to determine suture line stress. In other aspects, suture needle slip may be detected using an optical sensor or a force sensor.

In aspects, the needle driver tool may include an ultrasound transducer. The instructions, when executed by the processor, may cause the processor to display the position of the suture needle with respect to tissue based on data output from the ultrasound transducer. The needle driver tool may include an ultrasound transducer. The instructions, when executed by the processor, may cause the processor to determine the distance between the suture needle and a critical structure near the suture needle based on data output from the ultrasound transducer, and display, on a display, a message indicating the distance between the suture needle and the critical structure near the suture needle based on the data output from the ultrasound transducer.

The needle driver tool may include a sensor configured to sense a pull resistance on suture thread when pulling on the suture thread. The instructions, when executed by the processor, may cause the processor to determine that the pull force is greater than a threshold and reduce the pull force in response to determining that the pull force is greater than the threshold. The needle driver tool may include a sensor configured to sense a pull force on suture thread when tying a knot with the suture thread The instructions, when executed by the processor, may cause the processor to control the needle driver tool and the grasping tool to tie the knot with a predetermined pull force based on the sensed pull force.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An endoluminal robotic system comprising:
   at least one robotic arm;
   an endoscopic tool removably coupled to the at least one robotic arm, the endoscopic tool including an imaging device coupled to the distal end portion of the endoscopic tool;
   a needle driver tool removably coupled to the at least one robotic arm; and
   a grasping tool removably coupled to the at least one robotic arm;
   a processor; and
   a memory having stored thereon instructions, which, when executed by the processor, cause the processor to:
   receive a video image of a defect to be sutured from the imaging device;
   overlay a suture needle path including needle entry marks and needle exit marks on the video image;
   determine a position and an orientation of a suture needle; and
   control the at least one robotic arm to operate the needle driver tool and the grasping tool to drive the suture needle to suture the defect based on the suture needle path overlaid on the video image and the position and the orientation of the suture needle.

2. The endoluminal robotic system of claim 1, further comprising a force sensor coupled to the grasping tool,
   wherein the instructions, when executed by the processor, further cause the processor to:
   determine a force applied to tissue by the grasping tool based on force measurement data output from the force sensor; and
   generate an alert in response to determining that the force applied to tissue is greater than a predetermined force.

3. The endoluminal robotic system of claim 2, wherein the force sensor includes force sensors distributed in an array.

4. The endoluminal robotic system of claim 2, wherein the instructions, when executed by the processor, further cause the processor to:
   determine tissue type based on processing force measurement data output from the force sensor with a machine learning-based algorithm;
   receive grasping tool type information; and
   determine the predetermined force based on the tissue type and the grasping tool type information.

5. The endoluminal robotic system of claim 1, further comprising a force sensor coupled to the grasping tool,
   wherein the instructions, when executed by the processor, further cause the processor to:
   determine tissue type;
   acquire grasping tool type; and
   set a maximum force applied by the grasping tool based on the tissue type and the grasping tool type.

6. The endoluminal robotic system of claim 1, further comprising:
   an electromagnetic (EM) field generator configured to generate an EM field; and
   at least one EM sensor coupled to a suture needle,
   wherein the instructions, when executed by the processor, further cause the processor to track a position of the suture needle based on the EM field sensed by the at least one EM sensor.

7. The endoluminal robotic system of claim 1, wherein the instructions, when executed by the processor, further cause the processor to:
   detect slip of a suture needle; and
   control the at least one robotic arm to operate the endoscopic tool and/or the needle driver tool to account for the detected slip in response to detecting slip of the suture needle.

8. The endoluminal robotic system of claim 7, wherein detecting slip includes detecting movement of the suture needle with respect to the needle driver tool.

9. The endoluminal robotic system of claim 7, wherein the instructions, when executed by the processor, further cause the processor to:
   adjust the suture needle path based on the detected slip; and
   overlay the adjusted suture needle path on the received video image,
   wherein controlling the at least one robotic arm includes controlling the at least one robotic arm to operate the endoscopic tool and the needle driver tool based on the adjusted suture needle path overlaid on the video image.

10. The endoluminal robotic system of claim 7, further comprising a user controller, wherein the instructions, when executed by the processor, further cause the processor to provide haptic feedback to the user controller in response to detecting slip of the suture needle.

11. The endoluminal robotic system of claim 7, further comprising a user controller,
wherein the instructions, when executed by the processor, further cause the processor to generate vibrations in the user controller in response to detecting slip of the suture needle.

12. The endoluminal robotic system of claim 7, further comprising a pressure sensor,
wherein the instructions, when executed by the processor, further cause the processor to:
generate tissue tension data based on measurement data output from the pressure sensor; and
predict needle slip based on the tissue tension data.

13. The endoluminal robotic system of claim 1, wherein the instructions, when executed by the processor, further cause the processor to:
determine that the suture needle is near tissue; and
overlay a mark on the video image showing where the suture needle will exit tissue based on the position and the orientation of the suture needle in response to determining that the suture needle is near tissue.

14. The endoluminal robotic system of claim 13, wherein the instructions, when executed by the processor, further cause the processor to overlay a mark on the received video image showing a planned location where the suture needle will exit tissue.

15. The endoluminal robotic system of claim 13, wherein the instructions, when executed by the processor, further cause the processor to display structures to a side of or behind a suture location on the video image.

16. The endoluminal robotic system of claim 13, wherein the instructions, when executed by the processor, further cause the processor to display at least one of an entry location for the suture needle, the orientation of the suture needle, or a depth for the suture needle to avoid approaching structures.

17. The endoluminal robotic system of claim 13, wherein the instructions, when executed by the processor, further cause the processor to:
determine an amount of tissue resistance to movement of the suture needle; and
display the amount of the tissue resistance.

18. An endoluminal robotic system comprising:
an endoscopic tool including an imaging device coupled to the distal end portion of the endoscopic tool;
a needle driver tool;
a processor; and
a memory having stored thereon instructions, which, when executed by the processor, cause the processor to:
receive a video image from the imaging device;
overlay a suture needle path on the video image; and
control the needle driver tool to drive a suture needle based on the suture needle path overlaid on the video image;
detect slip of the suture needle by detecting, in the video image, motion of the suture needle independent of the motion of the needle driver tool;
adjust the suture needle path based on the detected slip;
overlay the adjusted suture needle path on the video image; and
control the needle driver tool based on the adjusted suture needle path overlaid on the video image.

19. A method comprising:
receiving a video image from a camera disposed on an endoscopic tool;
overlaying a suture needle path on the video image; and
controlling a robot to operate a driver tool to drive a suture needle based on the suture needle path overlaid on the video image;
detecting slip of the suture needle by detecting, in the video image, motion of the suture needle independent of the motion of the driver tool;
adjusting the suture needle path based on the detected slip;
overlaying the adjusted suture needle path on the video image; and
controlling the robot to operate the driver tool based on the adjusted suture needle path overlaid on the video image.

* * * * *